United States Patent
Kusumoto et al.

(10) Patent No.: US 8,299,129 B2
(45) Date of Patent: Oct. 30, 2012

(54) PEPTIDE LIPID-CONTAINING CARRIER AND METHOD FOR INTRODUCING COMPOUND INTO CELLS USING SAME

(75) Inventors: Kenichi Kusumoto, Kurume (JP); Itaru Hamachi, Kyoto (JP); Kazumi Sasamoto, Kumamoto (JP); Tetsuyuki Akao, Chikugo (JP); Munetaka Ishiyama, Kumamoto (JP); Takahiro Nagata, Kumamoto (JP); Chizu Ikeda, Kumamoto (JP); Takeshi Ido, Kumamoto (JP); Satoko Yamashita, Kurume (JP); Rieko Kuroda, Kurume (JP); Tomoyuki Ishikawa, Fukuoka (JP)

(73) Assignees: Fukuoka Prefectural Government, Fukuoka-shi (JP); Kyoto University, Kyoto-shi (JP); Dojindo Laboratories, Kamimashiki-gun (JP)

( * ) Notice: Subject to any disclaimer, the term of this patent is extended or adjusted under 35 U.S.C. 154(b) by 761 days.

(21) Appl. No.: 12/281,227

(22) PCT Filed: Mar. 1, 2006

(86) PCT No.: PCT/JP2006/304514
§ 371 (c)(1),
(2), (4) Date: Dec. 29, 2008

(87) PCT Pub. No.: WO2007/099650
PCT Pub. Date: Sep. 7, 2007

(65) Prior Publication Data
US 2009/0170960 A1     Jul. 2, 2009

(51) Int. Cl.
*A01N 25/00* (2006.01)
*A61K 47/00* (2006.01)
*A61K 38/06* (2006.01)
*C12N 5/00* (2006.01)
*C12N 5/02* (2006.01)
*C07K 5/00* (2006.01)
*C07K 7/00* (2006.01)
*C07K 16/00* (2006.01)
*C07K 17/00* (2006.01)

(52) U.S. Cl. ......... 514/773; 435/375; 514/785; 530/331

(58) Field of Classification Search ................ None
See application file for complete search history.

(56) References Cited

U.S. PATENT DOCUMENTS

| 3,808,190 A | 4/1974 | Dahlmans et al. |
| 3,953,417 A | 4/1976 | Konig et al. |
| 4,666,886 A | 5/1987 | Baschang et al. |
| 2003/0068379 A1 | 4/2003 | Li et al. |

FOREIGN PATENT DOCUMENTS

| DE | 21 60 042 | 6/1972 |
| DE | 28 06 954 A1 | 8/1979 |
| EP | 0 001 774 A1 | 5/1979 |
| EP | 0 114 787 A2 | 8/1984 |
| EP | 0 604 957 A1 | 7/1994 |
| EP | 0 638 588 A1 | 2/1995 |
| EP | 0 641 776 A2 | 3/1995 |
| GB | 1 374 588 | 11/1974 |
| JP | 51 095017 A | 8/1976 |
| JP | 04-221394 A | 8/1992 |
| JP | 05-320190 A | 12/1993 |
| WO | WO 03/101476 A1 | 12/2003 |

OTHER PUBLICATIONS

Hamachi et al. Protein Engineering Using Molecular Assembly: Functional Conversion of Cytochrome c via Noncovalent Interactions. J. Am. Chem Soc. 1997. vol. 119, pp. 9096-9102.*
Garg et al. Synthesis of glycopeptide derivatives containing the 2-acetamido-N-(L-aspart-4-oyl)-2-deoxy-β-D-glucopyranosylamine linkage and having the amino acid sequences 32-34, 33-35, 33-37, and 33-38 of bovine ribonuclease Carbohydrate Research. 1979, vol. 70, Issue 1, pp. 47-58.*
Kim et al. Gene-Transferring Efficiencies of Novel Diamino Cationic Lipids with Varied Hydrocarbon Chains. Bioconjugate Chem. 2004. vol. 15, pp. 1095-1101.*
Kortenaar et al. Synthesis of cytochrome C (66-104) nonatriacontapeptide and analogs. Peptides 1982., Proc Eur Pept Symp, 17, 1983. pp. 349-352.*
Stepanenko et al. The Synthesis of a Lipophilic Derivative of RGD Peptide. Russian Journal of Bioorganic Chemistry. 2004. vol. 30, No1. 2, pp. 111-113.*
Rosowsky et al., *Journal of Medicinal Chemistry*, 21(2): 170-175 (1978).
Toth et al., *Biochemical and Biophysical Research Communications*, 293: 18-22 (2002).

* cited by examiner

*Primary Examiner* — Marcela M Cordero Garcia
(74) *Attorney, Agent, or Firm* — Leydig, Voit & Mayer, Ltd.

(57) ABSTRACT

The present invention provides a carrier capable of highly efficiently introducing a compound into cells with low cytotoxicity, which contains peptide lipids represented by the following formula, and a method for introducing a compound into cells using the carrier: wherein $R^1$ is an amino acid or peptide having 1-10 amino acid residues, $R^2$ is a side chain of any amino acid, provided that $R^2$ has a carboxyl group, the carboxyl group may be an ester with a hydrocarbon group having 1-30 carbon atoms, $R^3$ is a hydrocarbon group having 1-30 carbon atoms.

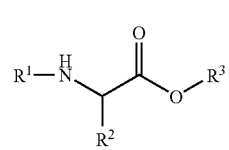

(I)

20 Claims, 8 Drawing Sheets

PEPTIDE LIPID-CONTAINING CARRIER AND METHOD FOR INTRODUCING COMPOUND INTO CELLS USING SAME

TECHNICAL FIELD

The present invention relates to a carrier consisting of peptide lipid-containing liposomes, which is suitable for efficiently introducing a compound such as a nucleic acid into cells, and a method for introducing a compound into cells using the same.

BACKGROUND ART

Recently, various diseases such as brain diseases, AIDS and genetic diseases have been intensely studied and many of their causative and related genes have been revealed. Accompanied therewith, great hopes have been placed on gene delivery aiming at elucidation of the function of a target gene in basic research fields, and gene therapy for diseases in advanced medical fields.

Calcium phosphate reagents, DEAE-dextran reagents, liposome reagents (e.g., Lipofectamine 2000, Lipofectin, etc.) and the like are known as reagents commercially available for gene delivery into cultured cells. In many cases, however, they are cytotoxic, show low introduction efficiency into normal cells and have a problem that introduction efficiency reduces in the presence of serum. Moreover, these reagents are not applicable to the gene delivery into experimental animals and human. While methods using a device such as microinjection method, electroporation method, particle bombardment (gene gun) method and the like, show relatively high introduction efficiency, there are problems that they require expensive devices and a lot of skill, throughput is low and the like. Since techniques for gene delivery using viral vectors have superior introduction efficiency into and gene expression capability in normal cells, they are attracting the highest attention in gene therapy. However, due to the pathogenicity (e.g., tumor induction) and immunogenicity of virus in vivo (inactivation by neutralizing antibody), a more safe gene delivery technique is desired.

The present inventors have studied and developed cationic lipids capable of introducing a plasmid DNA or an siRNA into cultured or primary cells with a high efficiency, and reported those that are suitable for introducing a plasmid (WO 2005/054486) and those that are suitable for introducing an siRNA (Japanese Patent Application No. 2004-356071) from their own repertoire of cationic lipids (JP-B-1984767). Furthermore, the present inventors have found that a gene can be introduced into cultured cells with a high efficiency using glycolipids (Japanese Patent Application No. 2005-080759).

DISCLOSURE OF THE INVENTION

It is an object of the present invention to provide a novel compound-carrier capable of inexpensively, easily, safely and efficiently introducing a compound into cells with low toxicity, and provide a method for introducing a compound into cells using the carrier without using special equipment.

To accomplish the above-mentioned objectives, the present inventors independently designed and synthesized a repertoire of peptide lipids (synthetic lipids tethering a peptide moiety), and found those that are suitable for introducing a plasmid DNA and those that are suitable for introducing an siRNA in the repertoire. These peptide lipids suitable for introducing a nucleic acid showed superior introduction efficiency even in the presence of 10% serum and low cytotoxicity compared to known introduction reagents using conjugated phospholipids. The present inventors conducted further investigations based on these findings, and reached the completion of the present invention.

Accordingly, the present invention provides:

(1) A compound represented by the following formula (I):

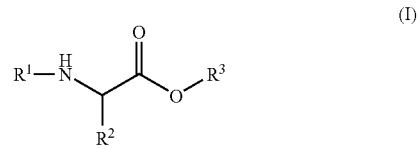

wherein $R^1$ is an amino acid or peptide having 1-10 amino acid residues, $R^2$ is a side chain of any amino acid, provided that $R^2$ has a carboxyl group, the carboxyl group may be an ester with a hydrocarbon group having 1-30 carbon atoms, and $R^3$ is a hydrocarbon group having 1-30 carbon atoms;

(2) the compound of (1) above, wherein $R^1$ is an amino acid or peptide having 1-5 amino acid residues;

(3) the compound of (1) or (2) above, wherein $R^1$ comprises one or more residues of at least one amino acid selected from the group consisting of Arg, Lys, Cys, Met, His, Tyr, Glu and Asp;

(4) the compound of (3) above, wherein the N-terminal amino acid of $R^1$ is selected from the group consisting of Arg, Lys, Cys, Met, His, Tyr, Glu and Asp;

(5) the compound of (4) above, wherein the N-terminal amino acid of $R^1$ is Arg or Lys;

(6) the compound of any of (1)-(5) above, wherein $R^2$ is —$CH_2COOR^4$ or —$C_2H_4COOR^4$ (wherein $R^4$ is a hydrocarbon group having 1-30 carbon atoms);

(7) the compound of (6) above, wherein $R^4$ is an unbranched alkyl or unbranched unsaturated hydrocarbon group having 10-20 carbon atoms;

(8) the compound of any of (1)-(7) above, wherein $R^3$ is an unbranched alkyl or unbranched unsaturated hydrocarbon group having 10-20 carbon atoms;

(9) a carrier for introducing a compound of interest into a cell, which comprises at least one of the compounds of (1)-(8) above;

(10) the carrier of (9) above, wherein the compound of interest is a nucleic acid;

(11) the carrier of (10) above, wherein the nucleic acid is a plasmid DNA, cDNA or antisense DNA, or an siRNA, miRNA, shRNA, mRNA, antisense RNA or RNA replicon;

(12) the carrier of (9) above, wherein the compound of interest is a peptide or protein;

(13) a complex of the carrier of any of (9)-(12) above and a compound of interest;

(14) a method for introducing a compound of interest into a cell, which comprises contacting the complex of (13) above with the cell; and

(15) a method for introducing a compound of interest into a cell within a human or non-human subject, which comprises administering the complex of (13) above to the subject.

By using the carrier for introducing a compound into cells of the present invention, the compound can be introduced into cells with a very high efficiency even in the presence of serum. In addition, since the peptide lipid of the present invention has a molecular structure degradable in cells and living tissues (biodegradability) which results in its low cytotoxicity, it is also superior to viral vectors and commercially available introduction reagents in the safety.

BEST MODE FOR CARRYING OUT THE INVENTION

Figure 1A:
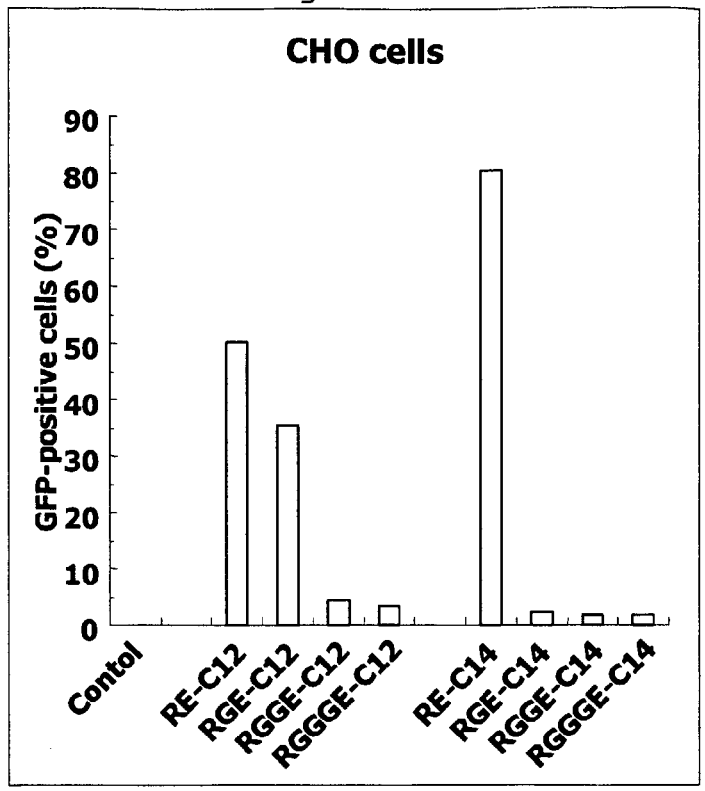
FIG. 1 shows an effect of head length of peptide lipids on introduction efficiency of plasmid DNA into CHO cells (FIG. 1A) and HC cells (FIG. 1B).

The carrier for introducing a compound into cells of the present invention (hereinafter to be also referred to as "the carrier of the present invention") is characterized in that it comprises a peptide lipid having a structure in which a head part consisting of any amino acid or peptide is ligated with a tail part consisting of any hydrocarbon chain via a connector part comprising any amino acid. To be specific, the carrier of the present invention is characterized in that it comprises a compound represented by the following formula (I):

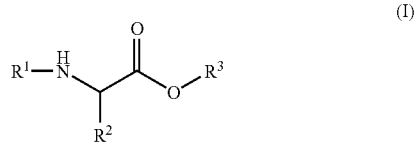

wherein $R^1$ is an amino acid or peptide having 1-10 amino acid residues, $R^2$ is a side chain of any amino acid, provided that $R^2$ has a carboxyl group, the carboxyl group may be an ester with a hydrocarbon group having 1-30 carbon atoms, and $R^3$ is a hydrocarbon group having 1-30 carbon atoms. Namely, $R^1$ corresponds to the head, —NHCH($R^2$)CO— corresponds to the connector and $OR^3$ corresponds to the tail.

Preferably, $R^1$ is an amino acid or peptide having 1-5 amino acid residues. The amino acid constituting $R^1$ may be 20 naturally occurring amino acids (Gly, Ara, Leu, Ile, Val, Arg, Lys, Glu, Gln, Asp, Asn, Cys, Met, His, Pro, Phe, Tyr, Thr, Ser, Trp), or modified or normative amino acids (e.g., 2-aminoadipic acid, 3-aminoadipic acid, β-alanine, 2-aminobutyric acid, 4-aminobutyric acid, 6-aminocaproic acid, 2-aminoheptanoic acid, 2,3-diaminopropionic acid, N-ethylglycine, N-ethylasparagine, hydroxylysine, norvaline, norleucine, ornithine and the like). When the amino acid has a carboxyl group (or carboxylate) at a position other than the C-terminus, the carboxyl group may be amidated or esterified. As examples of the ester used in this case, $C_{1-6}$ alkyl groups, for example, methyl, ethyl, n-propyl, isopropyl, n-butyl and the like; $C_{3-8}$ cycloalkyl groups, for example, cyclopentyl, cyclohexyl and the like; $C_{6-12}$ aryl groups, for example, phenyl, α-naphthyl and the like; phenyl-$C_{1-2}$ alkyl groups, for example, benzyl, phenethyl and the like; $C_{7-14}$ aralkyl groups, for example, α-naphthyl-$C_{1-2}$-alkyl groups such as α-naphthylmethyl; pivaloyloxymethyl groups; and the like can be mentioned.

Furthermore, the amino group of the N-terminal amino acid or any constituting amino acid of $R^1$ may be protected with a protecting group (for example, $C_{1-6}$ acyl groups such as $C_{1-6}$ alkanoyls such as formyl group and acetyl group); and a substituent (for example, —OH, —SH, amino group, imidazole group, indole group, guanidino group and the like) on the side chain of the amino acid in a molecule may be protected with an appropriate protecting group (for example, $C_{1-6}$ acyl groups such as $C_{1-6}$ alkanoyl groups such as formyl group and acetyl group, and the like).

$R^1$ may be an unbranched or branched (dendrimer type) peptide. For example, when $R^1$ comprises an amino acid having an amino group on its side chain such as Arg and Lys, a branched chain can be formed by binding the amino group with a carboxyl group of other amino acid or peptide. Since a dendrimer type peptide can have two or more Arg/Lys at the N-terminus, it can be more positively charged and advantageous when, for example, the peptide directly binds to a nucleic acid or protein having a negative charge. Also, when $R^1$ comprises an amino acid having a carboxyl group on its side chain such as Glu and Asp, a branched chain can be formed by binding the carboxyl group with an amino group of other amino acid or peptide. Furthermore, when $R^1$ comprises Cys, a branched chain can be formed via a disulfide bond between the Cys and other Cys or a peptide comprising the same.

In a preferable embodiment, $R^1$ can comprise a positively charged amino acid (e.g., Arg and Lys), in view that it can directly bind to a nucleic acid or protein having a negative charge.

In another preferable embodiment, $R^1$ can comprise an amino acid having a thiol group in the side chain (e.g., Cys), in view that it can bind to a thiolated nucleic acid or protein via a disulfide bond. The disulfide bond is reduced within a cell, and a compound of interest, nucleic acid or protein can be easily released. In addition, the behavior of the carrier itself in a tissue or cell and the structural change of the carrier when binding to a compound of interest such as nucleic acid can be observed by modifying the thiol group of Cys and the like with a fluorescent (e.g., FITC, rhodamine, Cy3, etc.).

In another preferable embodiment, $R^1$ can comprise an amino acid having an high affinity for a metal (e.g., Met and His), in view that it can bind to a nucleic acid and the like modified with a metal (e.g., chelation).

In another preferable embodiment, $R^1$ can comprise an amino acid having a hydroxyl group in the side chain (e.g., Thy, Thr and Ser), in view that it can bind to a functional group in the side chain of a compound of interest, nucleic acid or protein via a hydrogen bond and the like.

In another preferable embodiment, $R^1$ can comprise a negatively charged amino acid (e.g., Glu and Asp), in view that it can bind to a nucleic acid modified with a nucleic acid-binding protein and the like such as histone, which has a net positive charge due to the binding protein.

It is also preferable to use an amino acid other than those mentioned above as appropriate. For example, a signal peptide for cell recognition, a neurotransmitter γ-aminobutyric acid (GABA) or the like can be utilized to improve the interaction between the carrier and a target cell.

Preferably, $R^1$ comprises one or more residues of at least one amino acid selected from the group consisting of Arg, Lys, Cys, Met, His, Tyr, Glu and Asp. Although these amino acids can be placed at any positions in $R^1$ as long as they can interact with a compound of interest, nucleic acid or protein, or a target cell, it is desirable that at least one of them is placed at N-terminus. Therefore, the N-terminal amino acid of $R^1$ is preferably either Arg, Lys, Cys, Met, His, Tyr, Glu or Asp, more preferably Arg or Lys.

Examples of $R^2$ include the side chains of the naturally occurring amino acids or the modified or normative amino acids mentioned above for $R^1$, preferably, amino acids having a carboxyl group on the side chain, for example, Glu and Asp. More preferably, the peptide lipid of the present invention is a compound in which the carboxyl group on the side chain of the connector is esterified with a saturated or unsaturated alcohol having 1-30 carbon atoms. Namely, it is preferable that $R^2$ be —$CH_2COOR^4$ or —$C_2H_4COOR^4$, wherein $R^4$ is a hydrocarbon group having 1-30 atoms.

The term "hydrocarbon group" used herein includes hydrocarbon groups having 1-30 carbon atoms, for example, "alkyl group", "cycloalkyl group", "alkenyl group", "cycloalkenyl group", "alkynyl group", "aryl group", "aralkyl group", "cycloalkylalkyl group" and the like. These hydrocarbon groups may be substituted with one or more suitable substituents. Examples of such substituents include, but are not limited to, $C_1$-$C_6$ alkyl, $C_1$-$C_6$ alkenyl, $C_1$-$C_6$ alkynyl, $C_6$ aryl, $C_2$-$C_5$ heteroaryl, $C_3$-$C_6$ cycloalkyl, $C_1$-$C_6$ alkoxy, CN, OH, oxo, halo, COOH, $NH_2$, NH($C_1$-$C_6$ alkyl), N($C_1$-$C_6$ alkyl)$_2$, NH($C_6$ aryl), N($C_6$ aryl)$_2$, CHO, CO($C_1$-$C_6$ alkyl), CO($C_6$ aryl), COO($C_1$-$C_6$ alkyl), COO($C_6$ aryl), and the like.

Examples of "alkyl group" include, but are not limited to, "unbranched or branched $C_{1-30}$ alkyl groups" such as methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosanyl, henicosanyl, docosanyl, tricosanyl, tetracosanyl, pentacosanyl, hexacosanyl, heptacosanyl, octacosanyl, nonacosanyl, triacontyl and the like.

Examples of "cycloalkyl group" include, but are not limited to, "$C_{3-8}$ cycloalkyl groups" such as cyclopropyl, cyclobutyl, cyclopentyl, cyclohexyl, cycloheptyl, cyclooctyl and the like.

Examples of "alkenyl group" include, but are not limited to, "unbranched or branched $C_{2-30}$ alkenyl groups" such as vinyl, allyl, isopropenyl, 1-butenyl, 2-butenyl, 3-butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, henicosenyl, docosenyl, tricosenyl, tetracosenyl, pentacosenyl, hexacosenyl, heptacosenyl, octacosenyl, nonacosenyl, triacontenyl and the like.

Examples of "cycloalkenyl group" include, but are not limited to, "$C_{3-8}$ cycloalkenyl groups" such as cyclopropenyl, cyclobutenyl, cyclopentenyl, cyclohexenyl, cycloheptenyl, cyclooctenyl and the like.

Examples of "alkynyl group" include, but are not limited to, "unbranched or branched $C_{2-30}$ alkynyl groups" such as ethynyl, propynyl, 1-butynyl, 2-butynyl, 1-pentynyl, 2-pentynyl, 3-pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, icosynyl, henicosynyl, docosynyl, tricosynyl, tetracosynyl, pentacosynyl, hexacosynyl, heptacosynyl, octacosynyl, nonacosynyl, triacontynyl and the like.

Examples of "aryl group" include, but are not limited to, "$C_{6-14}$ aryl groups" such as phenyl, 1-naphthyl, 2-naphthyl, phenanthryl, anthryl and the like.

Examples of "aralkyl group" include, but are not limited to, "$C_{7-30}$ aralkyl group (i.e., $C_{6-24}$ aryl-$C_{1-6}$ alkyl group)" such as benzyl, phenethyl, 3-phenylpropyl, 4-phenylbutyl, (1-naphthyl)methyl, 2-(1-naphthyl)ethyl, 2-(2-naphthyl)ethyl and the like.

Examples of "cycloalkylalkyl group" include, but are not limited to, "$C_{3-8}$ cycloalkyl-$C_{1-6}$ alkyl groups" such as cyclopropylmethyl, cyclobutylmethyl, cyclopentylmethyl, cyclohexylmethyl, cycloheptylmethyl, cyclooctylmethyl, 2-cyclopropylethyl, 2-cyclobutylethyl, 2-cyclopentylethyl, 2-cyclohexylethyl, 2-cycloheptylethyl, 2-cyclooctylethyl and the like.

$R^3$ and $R^4$ are preferably unbranched saturated hydrocarbon groups having 10-20 carbon atoms (i.e., n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosanyl, n-henicosanyl, n-docosanyl, n-tricosanyl, n-tetracosanyl, n-pentacosanyl, n-hexacosanyl, n-heptacosanyl, n-octacosanyl, n-nonacosanyl and n-triacontyl) or unbranched unsaturated hydrocarbon groups (e.g., mono-unsaturated hydrocarbon groups such as trans-2-buten-1-yl, cis-9-tetradecen-1-yl, cis-9-hexadecen-1-yl, cis-9-octadecen-1-yl, cis-11-octadecen-1-yl, cis-9-eicosaen-1-yl, cis-13-docosaen-1-yl and cis-15-tetracosaen-1-yl, di-unsaturated hydrocarbon groups such as cis-9-cis-12-octadecdien-1-yl, tri-unsaturated hydrocarbon groups such as cis-9-cis-12-cis-15-octadectrien-1-yl and cis-9-cis-11-cis-13-octadectrien-1-yl, tetra-unsaturated hydrocarbon groups such as cis-4-cis-8-cis-12-cis-15-octadectetraen-1-yl and cis-5-cis-8-cis-11-cis-14-eicosatetraen-1-yl, penta-unsaturated hydrocarbon groups such as cis-7-cis-10-cis-13-cis-16-cis-19-docosapentaen-1-yl, hexa-unsaturated hydrocarbon groups such as cis-4-cis-7-cis-10-cis-13-cis-16-cis-19-docosahexaen-1-yl and the like). More preferably, $R^3$ and $R^4$ are unbranched alkyl having 12-16 carbon atoms (i.e., n-dodecyl, n-tridecyl, n-tetradecyl, n-pentadecyl and n-hexadecyl) or unbranched unsaturated hydrocarbon (e.g., cis-9-tetradecen-1-yl, cis-9-hexadecen-1-yl, cis-9-octadecen-1-yl, cis-9-octadecen-1-yl, cis-11-octadecen-1-yl, cis-9-eicosaen-1-yl, cis-13-docosaen-1-yl, cis-9-cis-12-octadecdien-1-yl, cis-9-cis-12-cis-15-octadectrien-1-yl, cis-9-cis-11-cis-13-octadectrien-1-yl, cis-4-cis-8-cis-12-cis-15-octadectetraen-1-yl, cis-5-cis-8-cis-11-cis-14-eicosatetraen-1-yl, cis-7-cis-10-cis-13-cis-16-cis-19-docosapentaen-1-yl, cis-4-cis-7-cis-10-cis-13-cis-16-cis-19-docosahexaen-1-yl and the like) groups having 10-20 carbon atoms. $R^3$ and $R^4$ can be the same group.

As specific examples of the compounds represented by the formula (I), the following compounds:

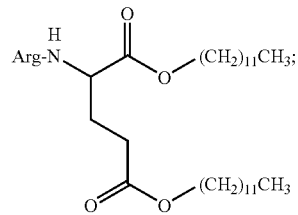

(RE-C12)

(RGE-C12)
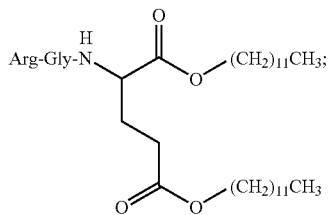

(RE-C14)
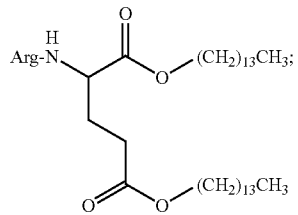

(KE-C14)
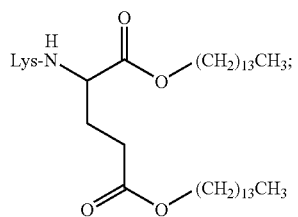

(RGD-C12)
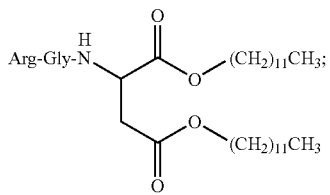

(RE-C16)
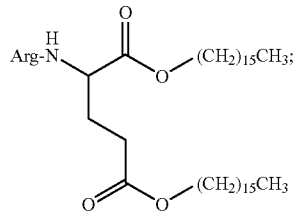

(KEC18-oleyl)
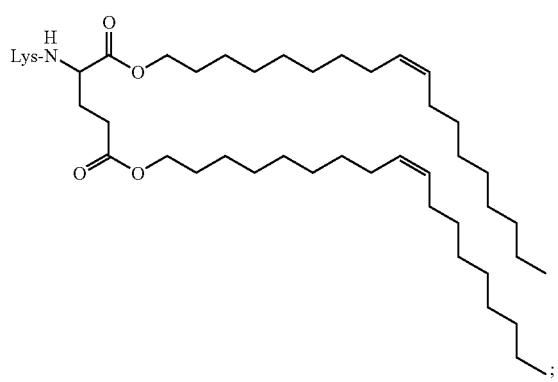

(R₂KE-C12)
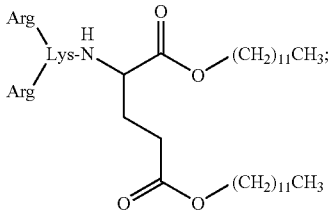

((RG)₂KE-C12)
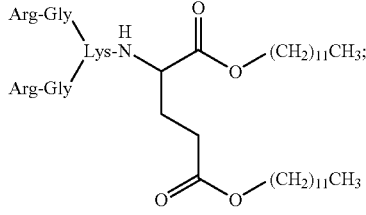

(KE-C12)
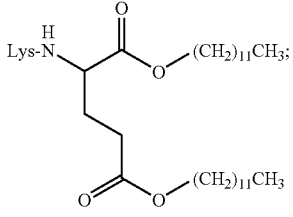

(KGE-C12)
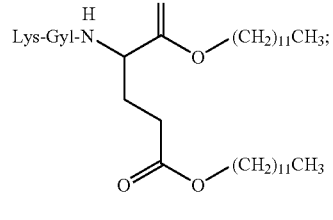

(KE-C18)
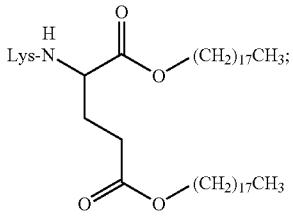

and the like are exemplified, but not limited thereto.

The compound represented by the formula (I) can be manufactured by combining a known peptide synthesis method and an esterification method. For example, the α-carboxyl group of amino acid ($NH_2$—$CH(R^2)$—COOH) of the connector of is condensed with a desired alcohol ($R^3$—OH) to prepare an amino acid ester, and then a peptide chain can be extended onto the amino group side of the amino acid ester to synthesize $R^1$ peptide, or the amino acid ester can be condensed with previously synthesized $R^1$ peptide. The method of peptide synthesis may, for example, be any of solid phase synthesis and liquid phase synthesis. $R^1$ peptide can be produced by condensing a partial peptide or amino acid that constitutes $R^1$ and the remaining part, and, when the product has a protecting group, removing the protecting group. Here, condensation and removal of the protecting group can be achieved by methods known per se, for example, the methods described in (i) and (ii) below.

(i) M. Bodanszky and M. A. Ondetti: Peptide Synthesis, Interscience Publishers, New York (1966)
(ii) Schroeder and Luebke: The Peptide, Academic Press, New York (1965)

Specifically, for example, the compound can be synthesized according to the method disclosed in Kanegae and Akao ("Design and Synthesis of the Artificial Peptide-Lipids Having Adamantane Group", in *The Research Reports of Fukuoka Industrial Technology Center in* 1998, pp. 113-116).

The carrier of the present invention comprises either one species of the above-mentioned peptide lipid molecules. Also, the carrier may comprise two or more species of the above-mentioned peptide lipid molecules in combination. Furthermore, the carrier may further comprise a molecule other than the above-mentioned peptide lipid molecule, for example, amphiphilic molecule (e.g., phospholipid derived from biomembrane such as phosphatidylinositol, phosphatidylserine, phosphatidylethanolamine, phosphatidylcholine, etc.), cationic lipid molecule, surfactant (e.g., CHAPS, sodium cholate, octylglucoside, N-D-gluco-N-methylalkanamide, etc.), polyethylene glycol, glycolipid, peptide lipid, protein or the like, as long as it does not lose the advantages of the present invention such as high introduction efficiency of a compound of interest into cells and low cytotoxicity.

The carrier of the present invention is provided as an assembly in which the above-mentioned peptide lipid molecules are organized, or in the form in which the above-mentioned peptide lipid molecules are completely dispersed in a dispersion medium (i.e., solution or suspension). "Organization" means that the carrier-constituting molecules including the peptide lipids assemble each other via non-covalent bonds such as hydrophobic bond. Examples of the organized assembly include bilayer membrane formed by hydrophobic bonding between the hydrophobic parts of the carrier-constituting molecules, liposome, multilayer vesicle, ribbon-shaped assembly, disc-shaped assembly, lamellar assembly, rod-shaped assembly and the mixture thereof. Examples of the dispersion medium to completely disperse the carrier-constituting molecules include organic solvents such as ethanol, methanol and DMSO.

The carrier of the present invention can be prepared as an assembly of molecules by dispersing the above-described peptide lipid molecules in an appropriate dispersion medium, for example, an aqueous solvent, and, if required, performing an operation to induce organization. Examples of the "operation to induce organization" include, but are not limited to, various methods known per se, such as sonication, heating, vortexing, ether injection, French press method, cholic acid method, $Ca^{2+}$ fusion, freezing and thawing method, and reversed phase evaporation [details of these methods are given in, for example, Chapter 2: Preparation of Liposomes (written by Sunamoto and Iwamoto) in "Liposomes", Nojima, Sunamoto, and Inoue, eds. (Nankodo, published in 1988), and elsewhere]. Under particular conditions, it is also possible to allow the carrier-constituting molecules including a peptide lipid to autonomously assemble in an aqueous solvent to form an assembly (self-organize) without performing the operation to artificially induce organization described above. Although the assembly obtained by self-organization is normally a mixture of the various forms described above, it is also possible to form an assembly in a single form by performing the operation to induce organization described above under particular conditions.

Alternatively, the carrier of the present invention can be prepared in a completely dispersed molecule state by dissolving the above-described peptide lipid molecules in a solution containing an organic solvent such as ethanol, methanol, or DMSO.

A species of the above-described peptide lipid molecules can be chosen as appropriate according to the compound introduced (herein also referred to as "the compound of interest"); examples of choosable compounds include, but are not limited to, the above-described RE-C12, RGE-C12, RE-C14, RE-C16, KE-C14, KE-oleyl and the like when a plasmid DNA is introduced, and RE-C12, RGE-C12, RGGE-C12, RE-C14, RGD-C12 and the like when siRNA is introduced.

The mixing ratio of the above-described peptide lipid molecules used for preparing the carrier of the present invention is not subject to limitation, and is, for example, about 0.01 to 10, preferably about 0.1 to 1, based on the molar ratio to all carrier-constituting molecules.

In a preferred mode of embodiment, the above-described peptide lipid molecules used for preparing the carrier of the present invention are solid, gel, liquid and the like, which, however, are not to be construed as limiting the invention. Examples of the dispersion medium for dispersing the peptide lipid molecules include, but are not limited to, an aqueous solvent such as water (deionized water and the like), saline, phosphate-buffered saline (PBS), or a medium used by those skilled in the art for ordinary cell culture (e.g., RPMI1640, DMEM, HAM F-12, Eagle's medium and the like), an organic solvent such as ethanol, methanol, or DMSO, a mixed solvent of an aqueous solvent and an organic solvent, and the like. Although the aqueous solvent is preferably free from protein components such as serum, it is also possible to prevent the inhibition of the organization of the carrier-constituting molecules including peptide lipid molecules, or the subsequent complex formation between the compound introduced into cells and the assembly of peptide lipid molecules, by removing the protein components by polylysine treatment and the like in advance. When the compound introduced into cells is a nucleic acid such as an RNA or a DNA, or a peptidyl compound such as an oligopeptide or a protein, the stability of the compound of interest decreases due to the minglement of a nucleic-acid-decomposing enzyme such as RNase or DNase or a protein-(peptide)-decomposing enzyme such as peptidase or protease; therefore, the aqueous solvent preferably undergoes heat treatment to inactivate these enzymes before the peptide lipid molecules are dispersed. Examples of the heat treatment include, but are not limited to, a treatment at about 50 to about 100° C. for about 5 minutes to about 3 hours. Accordingly, the aqueous solvent is preferably one that permits the heat treatment. Various culture broths conventionally used for introducing a nucleic acid to cells often do not permit the removal of enzymes such as RNase; however, even when dispersed in an aqueous solution containing a compound such as NaCl or potassium chloride, the peptide lipid molecules in the present invention exhibits high introduction efficiency in the subsequent operation of intracellular introduction. Accordingly, when a compound such as a nucleic acid or a peptidyl compound is introduced into cells, the aqueous solvent is preferably an aqueous solution containing the above-described compound and the like.

Although the pH of the aqueous solvent is not subject to limitation, it is preferably in the range of pH 4 to 10, more preferably in the range of pH 6 to 8.

In preferred modes of embodiment, a peptide-lipid-containing liposome is prepared by (1) sonication or (2) heat treatment as described in detail below.
(1) Sonication Method First, the above-described peptide lipid molecules are dissolved in an organic solvent (e.g., chloroform and the like), and the resulting solution is placed in a container such as an eggplant-shaped flask; the solvent is evaporated off under reduced pressure using a rotary evaporator and the like to form a thin membrane of lipid on the container wall surface. An aqueous solvent (e.g., phosphate buffer solution (pH 7.0) and the like) is added to the membrane, followed by shaking to swell the membrane, which is then detached using, for example, a vortex mixer and the like, to yield a suspension of multilayer liposome. To remove the decomposed lipids and the like, gel filtration may be performed using a Sephadex 2B, 4B or G-50 column and the like.

By sonicating the resulting suspension of multilayer liposome at a high output (e.g., about 100 to about 200 W) on an ice bath or water bath using a sonicator (probe type, bathtub type and the like) for about 1 to about 2 minutes (e.g., a cycle of 1-minute sonication and 30-second interval repeated about two to four times and the like), a nearly uniform monolayer liposome can be prepared.

In the peptide lipid molecules of the present invention, a peptide-lipid-containing liposome can easily be prepared solely by transferring an appropriate amount of a powder thereof to a tube, adding MiliQ water and the like (to obtain a final concentration of about 20 mM), and performing the same sonication as described above.

(2) Heat Treatment Method

A peptide-lipid-containing liposome can be prepared by transferring an appropriate amount of a powder of the above-described peptide lipid molecules to a tube, adding MiliQ water and the like (to obtain a final concentration of about 20 mM), and heating the mixture at about 90° C. for about 15 minutes.

The peptide lipid molecule concentration in the peptide-lipid-containing liposome obtained can be set as appropriate in consideration of the kind of peptide lipid molecules used and the like, and is normally in the range of 1 to 200 mM, preferably 1 to 100 mM, and more preferably 1 to 50 mM.

If the concentration is too low, no sufficient amount of peptide-lipid-containing liposome is formed; if the concentration is too high, the peptide lipid molecules can precipitate.

The carrier of the present invention may contain an appropriate additive, as long as the addition thereof does not affect any of the advantages of the invention, such as the high efficiency of compound introduction to cells and the low cytotoxicity. When the carrier of the present invention is used for the purpose of introducing a compound into cells of a living body, the additive must be a pharmaceutically acceptable one. For example, various pharmaceutical additives for formulation in conventionally known liposome preparations can be used.

The carrier of the present invention, which can be obtained as described above, is useful as a drug for efficiently introducing a compound into cells at low toxicity. Any compound can be introduced into cells using the carrier of the present invention; for example, nucleic acids, peptides, lipids, peptide lipids, sugars, bioactive substances, drugs (doxorubicin (antitumor drug), daunorubicin (antitumor drug), vincristine (antitumor drug), vinblastine (antitumor drug), idarubicin (antitumor drug), dibucaine (local anesthetic), propranolol (β blocker), quinidine (antiarrhythmic therapeutic), dopamine (cardiotonic hypertensive), imipramine (antidepressant), diphenhydramine (antihistamine), quinine (antimalarial), chloroquine (antimalarial), diclofenac (anti-inflammatory drug) and the like), moisturizers for cosmetics and the like (mannitol and the like), other synthetic or natural compounds and the like can be mentioned.

A particularly preferable compound that can be introduced into cells using the carrier of the present invention is a nucleic acid. Any nucleic acid can be used, whether it is a DNA, an RNA, a DNA-RNA chimeric nucleic acid, a DNA/RNA hybrid or the like. Although the nucleic acid may be single-stranded to triple-stranded, it is preferably single-stranded or double-stranded. The nucleic acid may be another type of nucleotide that is an N-glycoside of the purine or pyrimidine base, or another oligomer having a non-nucleotide skeleton (e.g., commercially available peptide nucleic acid (PNA) and the like) or another oligomer containing a special bond (however, the oligomer contains a nucleotide having an arrangement that allows base pairing or base attachment as found in DNA and RNA) and the like. Furthermore, the nucleic acid may also be one having a known modification added thereto, for example, one with a marker known in the art, one with a cap, one methylated, one having one or more naturally occurring nucleotides substituted by analogues, one modified with an intramolecular nucleotide, for example, one having a non-charge bond (e.g., methylphosphonate, phosphotriester, phosphoramidate, carbamate and the like), one having a charged bond or a sulfur-containing bond (e.g., phosphorothioate, phosphorodithioate and the like), for example, one having a side chain group of a protein (nuclease, nuclease inhibitor, toxin, antibody, signal peptide, poly-L-lysine and the like), a sugar (e.g., monosaccharide and the like) and the like, one having an intercalating compound (e.g., acridine, psoralen and the like), one containing a chelate compound (e.g., metals, radioactive metals, boron, oxidizing metals and the like), one containing an alkylating agent, or one having a modified bond (e.g., α anomer type nucleic acid and the like).

For example, any kind of DNA can be chosen as appropriate according to the purpose of use; examples include plasmid DNA, cDNA, antisense DNA, chromosome DNA, PAC, BAC and the like, with preference given to plasmid DNA, cDNA and antisense DNA, more preferably plasmid DNA. A circular DNA such as plasmid DNA can also be used as a linear DNA after being digested as appropriate with a restriction endonuclease and the like. Also, any kind of RNA can be chosen as appropriate according to the purpose of use; examples include siRNA, miRNA, shRNA, antisense RNA, messenger RNA, single strand RNA genome, double strand RNA genome, RNA replicon, transfer RNA, ribosomal RNA and the like, with preference given to siRNA, miRNA, shRNA, mRNA, antisense RNA and RNA replicon.

The size of the nucleic acid is not subject to limitation; although a broad range of nucleic acids, from giant nucleic acid molecules (e.g., about $10^7$ kbp in size) such as chromosomes (artificial chromosome and the like) to low-molecular nucleic acids (e.g., about 5 bp in size), can be introduced, the size is preferably not more than 15 kbp in consideration of the efficiency of nucleic acid introduction into cells. For example, the size of a high-molecular nucleic acid like plasmid DNA is exemplified by 2 to 15 kbp, preferably 2 to 10 kbp. The size of a low-molecular nucleic acid like siRNA is exemplified by 5 to 1000 bp, preferably 5 to 500 bp, and more preferably 5 to 200 bp.

The nucleic acid may be a naturally occurring one or a synthetic one; provided that the size is not more than about 100 bp, the nucleic acid can be synthesized by the phosphotriethyl method, the phosphodiester method and the like using a commonly used automated nucleic acid synthesizer.

Although the nucleic acid used in the present invention is not subject to limitation, it is preferably purified by a method commonly used by those skilled in the art.

Examples of modes of embodiment wherein the carrier of the present invention is used to introduce a prophylactic and/or therapeutic (hereinafter abbreviated as "prophylactic/therapeutic") compound into cells of a living body include the use of a compound for the prevention and/or treatment, including what is called gene therapy, in administration in vivo, intended to prevent and/or treat a disease. Accordingly, in a preferred mode of embodiment of the present invention, the compound introduced into cells using the carrier of the invention possesses prophylactic/therapeutic activity for a particular disease. Examples of such compounds include nucleic acids, peptides, lipids, sugars, bioactive substances, drugs, and other natural or synthetic compounds.

As described above, gene therapies can be roughly divided into those intended to supplement lacked genetic information and those intended to control the expression of the causal gene (target gene) for a disease.

For example, when the compound capable of controlling the expression of the target gene is a low-molecular nucleic acid, the low-molecular nucleic acid is exemplified by siRNA, miRNA, an antisense oligonucleotide, ribozyme, a decoy oligonucleotide (e.g., an oligonucleotide comprising a base sequence that can be recognized and bound by a transcription factor or a transcription suppression factor) and the like.

When the compound capable of controlling the expression of the target gene is a peptide or a protein, the peptide/protein is exemplified by a peptide/protein that binds to the target gene to control the transcription of the gene, or that binds to the mRNA or initial transcription product of the target gene to control the translation thereof into a protein, or a peptidyl ligand capable of enhancing a signal from a receptor that controls the expression of the target gene, or an antagonist-like peptide/protein capable of blocking the signal, and the like.

Alternatively, the compound possessing prophylactic/therapeutic activity for a disease may be one capable of controlling the activity of the causal protein for the disease. Examples of such compounds include, but are not limited to, peptides/proteins that are ligands for the target receptor protein, non-peptidyl compounds (e.g., fatty acids, steroid hormones and the like), various natural or synthetic compounds possessing agonist or antagonist activity, peptides that mimic a partial amino acid sequence of the phosphorylation site of kinase and the like.

The present invention also provides a complex of the carrier of the invention and a compound to be introduced into cells, preferably a compound as mentioned above.

When the above-described carrier is used to introduce a compound into cells, the carrier and the compound of interest are brought into contact with each other to form a complex of the carrier and the compound of interest (hereinafter also simply referred to as "complex"). The complex may be formed by any interaction, as long as the complex can be stably present, and as long as the decomposition of the compound of interest (nucleic acid, peptide and the like) by, for example, nuclease, peptidase and the like, is be suppressed. For example, when the compound of interest is a negatively charged compound such as a nucleic acid or a peptide, a complex can be formed via a non-covalent bond based on an electrostatic interaction using a carrier containing a positively charged peptide lipid. When the compound of interest is positively charged or non-charged, a complex can be formed via a non-covalent bond based on an electrostatic interaction using a carrier containing a negatively charged peptide lipid. Alternatively, a complex with the carrier can also be formed by interlaying another interaction, or by binding the compound of interest to a negatively charged compound in advance. Examples of other interactions include, but are not limited to, the above-described interactions with respect to the preferred mode of embodiment of the constituent amino acids for $R^1$.

Regarding the form of the complex, when the carrier is a liposome, for example, the compound may be in a form bound to the liposome or in a form incorporated in the liposome, preferably in a form incorporated in the liposome.

The above-described complex of a carrier and the compound of interest is obtained by mixing an aqueous solvent containing the carrier and the compound of interest, and incubating the mixture. The kind of the aqueous solvent is the same as described above.

Temperature during the incubation is preferably set over the same range of temperature as in the above-described method of preparing a peptide-lipid-containing liposome.

The concentration of the above-described carrier in the mixture can be set as appropriate in consideration of the kind of peptide lipid molecules used and the like, and is normally in the range of 1 to 200 mM, preferably 1 to 100 mM, more preferably 1 to 50 mM, still more preferably 5 to 50 mM, and most preferably 10 to 30 mM.

If the concentration is too low, no sufficient amount of stable complex is formed; if the concentration is too high, the carrier can precipitate.

The concentration of the compound of interest in the mixture can be set as appropriate in consideration of the kind and size (molecular weight) of the compound used and the like; when the compound is a nucleic acid, its concentration is normally in the range of about 0.01 to about 100 ng/μL.

When the compound is a DNA, its concentration is normally in the range of 3 to 100 ng/μL. For example, when the DNA is an ordinary plasmid DNA (about 3 kbp in size), the DNA concentration in the mixture is preferably in the range of 10 to 90 ng/μL, more preferably 20 to 80 ng/μL, still more preferably 30 to 70 ng/μL, and most preferably 40 to 60 ng/μL.

If the concentration is too low, the DNA introduced into cells cannot exhibit the expected function; if the concentration is too high, nucleic acid introduction efficiency decreases on the contrary.

Even when the compound is an RNA, its concentration can be set as appropriate in consideration of the size of the RNA and the like; when the size of the RNA is about several kilobase pairs, the RNA concentration in the above-described mixture is normally in the range of 3 to 100 ng/μL, preferably 10 to 90 ng/μL, more preferably 20 to 80 ng/μL, still more preferably 30 to 70 ng/μL, and most preferably 40 to 60 ng/μL.

In particular, when the nucleic acid is as small as about 20 to about 200 bp like siRNA, the concentration of the nucleic acid is normally in the range of 1 to 500 nM, preferably 20 to 400 nM, more preferably 20 to 300 nM, still more preferably 20 to 200 nM, and most preferably 20 to 100 nM.

If the concentration is too low, the RNA introduced into cells cannot exhibit the expected function; if the concentration is too high, nucleic acid introduction efficiency decreases on the contrary.

Incubation time after mixing the aqueous solvent containing the carrier and the compound of interest can be set as appropriate in consideration of the kind of reagent used and other conditions, and is normally in the range of 0.5 to 500 minutes, preferably 0.5 to 200 minutes, more preferably 0.5 to 120 minutes, still more preferably 0.5 to 60 minutes, and most preferably 1 to 45 minutes.

If the incubation time is too short, complex formation between the compound of interest and the carrier is insufficient; if the incubation time is too long, the complex formed becomes unstable in some cases; in both cases, introduction efficiency for the compound of interest decreases.

By the above-described step, a mixture containing the carrier used to introduce the compound of interest into cells and the compound (hereinafter also described as "complex-containing solution") can be obtained.

Furthermore, by bringing the complex obtained in the above-described step and cells into contact with each other, the compound of interest contained in the complex can be introduced into the cells.

Although the kind of the above-described "cells" is not subject to limitation, whether they are derived from a prokaryote or a eukaryote, a eukaryote is preferred. The kind of eukaryote is also not subject to limitation, and is exemplified by vertebrates such as mammals, including humans (humans, monkeys, mice, rats, hamsters, cattle and the like), birds (chickens, ostriches and the like), amphibians (frogs and the like), and fishes (zebrafish, killifish and the like), invertebrates such as insects (silkworms, moths, drosohilas and the like), plants, microorganisms such as yeast, and the like. More preferably, the subject cells in the present invention are animal or plant cells, more preferably mammalian cells.

The cells may be cells of a cultured cell line, including cancer cells, cells isolated from an individual or a tissue, or cells of a tissue or a tissue fraction. The cells may also be adherent cells or non-adherent cells.

The step for bringing the complex and the cells into contact with each other can be described in more detail below.

The cells are suspended in an appropriate medium several days before contact with the complex, and cultured under appropriate conditions. At the time of contact with the complex, the cells may be in the logarithmic phase or not.

Although the culture broth used at the time of contact may be a serum-containing medium or a serum-free medium, it is preferable that the serum concentration in the medium be not more than 30%, preferably not more than 20%. This is because the presence of a protein such as serum in excess in the medium can inhibit the contact of the complex and the cells.

Cell density at the time of the contact is not subject to limitation, and can be set as appropriate in consideration of the kind of cells and the like, normally in the range of $0.1 \times 10^5$ to $5 \times 10^5$ cells/mL, preferably $0.1 \times 10^5$ to $4 \times 10^5$ cells/mL, more preferably $0.1 \times 10^5$ to $3 \times 10^5$ cells/mL, still more preferably $0.2 \times 10^5$ to $3 \times 10^5$ cells/mL, and most preferably $0.2 \times 10^5$ to $2 \times 10^5$ cells/mL.

The complex-containing solution described above is added to the cell-containing medium thus prepared. The amount of complex-containing solution added is not subject to limitation, and can be set as appropriate in consideration of cell count and the like, normally in the range of 1 to 1000 μL, preferably 1 to 500 μL, more preferably 1 to 300 μL, still more preferably 1 to 200 μL, and most preferably 1 to 100 μL, per milliliter of the medium.

After the complex-containing solution is added to the medium, the cells are cultured. Temperature, humidity, $CO_2$ concentration and the like during the cultivation are set as appropriate in consideration of the kind of cells. In the case of mammalian cells, normal conditions are about 37° C. temperature, about 95% humidity, and about 5% $CO_2$ concentration.

Cultivation time can also be set as appropriate in consideration of the kind of cells used and other conditions, and is normally in the range of 1 to 72 hours, preferably 1 to 60 hours, more preferably 1 to 48 hours, still more preferably 1 to 40 hours, and most preferably 1 to 32 hours.

If the above-described cultivation time is too short, introduction of the compound of interest into the cells is insufficient; if the cultivation time is too long, the cells can become less vigorous.

The compound is introduced into the cells by the above-described cultivation; preferably, the cultivation is continued with the medium replaced with a fresh medium, or with a fresh medium added to the medium. When the cells are of mammalian origin, the fresh medium preferably contains serum or a nutritive factor.

Time for the further cultivation can be set as appropriate in consideration of the expected function of the compound introduced and the like; when the compound is a plasmid DNA such as an expression vector, the time is normally in the range of 8 to 72 hours, preferably 8 to 60 hours, more preferably 8 to 48 hours, still more preferably 8 to 36 hours, and most preferably 12 to 32 hours. When the compound is a low-molecular nucleic acid capable of controlling the expression of a target gene such as siRNA, the time is normally in the range of 0 to 72 hours, preferably 0 to 60 hours, more preferably 0 to 48 hours, still more preferably 0 to 36 hours, and most preferably 0 to 32 hours.

As described above, by using a complex of the carrier of the present invention and a compound, the compound can be introduced into cells not only in vitro, but also in vivo. Hence, by administering the complex to a recipient, the complex reaches and comes in contact with target cells, thus resulting in the in vivo introduction of the compound contained in the complex into the cells.

The recipient to which the complex can be administered is not subject to limitation, and is exemplified by vertebrates such as mammals, including humans (humans, monkeys, mice, rats, hamsters, cattle and the like), birds (chickens, ostriches and the like), amphibians (frogs and the like), and fishes (zebrafish, killifish and the like), invertebrates such as insects (silkworms, moths, drosophilas and the like), plants and the like. Preferably, the recipient of the complex is a human or another mammal.

The method of administering the complex is not subject to limitation, as long as the complex reaches and comes in contact with target cells to allow the compound of interest contained in the complex to be introduced into the cells; a method of administration known per se (oral administration, parenteral administration (intravenous administration, intramuscular administration, topical administration, percutaneous administration, subcutaneous administration, intraperitoneal administration, spraying and the like) and the like) can be chosen as appropriate in consideration of the kind of compound of interest, the kind and site of target cells, and the like.

The dosage of the complex is not subject to limitation, as long as introduction of the compound into the cells is accomplishable, and can be chosen as appropriate in consideration of the kind of recipient, the method of administration, the kind of compound of interest, the kind and site of target cells, and the like. In the case of oral administration, the usual dosage per administration for a human (weighing 60 kg), for example, is about 0.001 mg to 10000 mg, based on the complex. In the case of parenteral administration (e.g., intravenous administration and the like), the usual dosage per administration for a human (weighing 60 kg), for example, is about 0.0001 mg to 3000 mg, based on the complex. In the case of another animal, a dosage converted per 60-kg body weight can be administered.

Because the use of the carrier of the present invention makes it possible to introduce a compound into cells at very high efficiency, the present invention provides an agent containing the carrier for introducing a compound into cells in vitro or in vivo. The agent can be provided as a research reagent, a pharmaceutical and the like. By using the agent in the method described above, a desired compound can easily be introduced into cells.

When the carrier of the present invention is used as an agent for introducing a compound into cells, it can be prepared as a formulation by a conventional method.

When the agent is provided as a research reagent, the carrier of the present invention can be provided as is, or as, for example, a sterile solution or suspension in water or other physiologically acceptable liquid (e.g., the above-described water-soluble solvent, an organic solvent such as ethanol, methanol and DMSO, a mixture of the water-soluble solvent and the organic solvent, and the like). The agent can contain as appropriate physiologically acceptable additives known per se, such as a filler, a vehicle, an antiseptic, a stabilizer, and a binder.

When the agent is provided as a pharmaceutical, the carrier of the present invention can be produced as an oral preparation (e.g., tablets, capsules and the like) or a parenteral preparation (e.g., injectable preparations, sprays and the like), as is, or as a blend with known pharmaceutically acceptable additives such as a carrier, a flavoring agent, a filler, a vehicle, an antiseptic, a stabilizer, and a binder, in a unit dosage form required for generally accepted preparation design.

Examples of additives that can be blended in tablets, capsules and the like include binders like gelatin, cornstarch, tragacanth and acacia, fillers like crystalline cellulose, swelling agents like cornstarch, gelatin, alginic acid and the like, lubricants like magnesium stearate, sweeteners like sucrose, lactose or saccharin, flavoring agents like peppermint, akamono oil or cherry, and the like can be used. When the formulation unit form is a capsule, the above-described type of material can further contain a liquid carrier like an oil or fat. The aqueous solution for injectable preparations is exemplified by saline, isotonic solutions containing glucose and another auxiliary (e.g., D-sorbitol, D-mannitol, sodium chloride and the like) and the like, and may be used in combination with an appropriate solubilizer, for example, an alcohol (e.g., ethanol), a polyalcohol (e.g., propylene glycol, polyethylene glycol), a non-ionic surfactant (e.g., Polysorbate 80™, HCO-50) and the like. The oily liquid is exemplified by sesame oil, soybean oil and the like, and may be used in combination with a solubilizer such as benzyl benzoate or benzyl alcohol.

The above-described agent may also be formulated with, for example, a buffering agent (e.g., phosphate buffer solution, sodium acetate buffer solution), a soothing agent (e.g., benzalkonium chloride, procaine hydrochloride and the like), a stabilizer (e.g., human serum albumin, polyethylene glycol and the like), a preservative (e.g., benzyl alcohol, phenol and the like), an antioxidant (e.g., ascorbic acid and the like) and the like.

The amount of the carrier of the present invention contained in these agents is not subject to limitation, as long as introduction of compound into cells is accomplishable when the carrier is used in the above-described method; the amount can be chosen as appropriate according to the kind of dosage form, the kind of compound introduced and the like.

Alternatively, the carrier contained in the agent of the present invention may be a complex with a compound desired to be introduced into cells.

The carrier of the present invention can also be provided as a kit for introducing a compound into cells. The kit can further comprise any reagent that can be used in the method of introducing a compound into cells using the carrier of the present invention, and the like (e.g., the above-described aqueous solvent, instruction sheet bearing the preparation protocol, reaction vessel and the like). By using the kit, a desired compound can easily be introduced into cells according to the method described above.

EXAMPLES

The present invention is explained in detail in the following by referring to Examples, which are not to be construed as limitative in any way.

Example 1

Synthesis and Preparation of Peptide Lipid (1) Synthesis of Peptide Lipid (Synthesis Method of RE-C12)

Amino acid (L-glutamic acid; E), fatty alcohol (dodecyl alcohol; C12-OH) and p-toluenesulfonic acid were mixed in a toluene solvent, and the mixture was heated under reflux in a reaction vessel equipped with a Dean-Stark trap. An ester bond was formed by dehydrative condensation. Crystals of p-toluenesulfonate of E-C12 were precipitated by cooling (4° C.), collected by filtration and washed with cold toluene to give white crystals. Then, amino acid protected with Boc (Boc-Arg(Boc)$_2$-OH) was condensed with E-C12 in a dimethylformamide solvent in the coexistence of HOBt, WSC and TEA. The synthesized substance (Boc-Arg(Boc)$_2$-Glu-C12) was purified by silica gel column chromatography, and the Boc protection was removed with trifluoroacetic acid to give Arg-Glu-C12(RE-C12). NMR was used for identification. Other peptide lipids were synthesized by a similar method.

(2) Preparation of Aqueous Peptide Lipid Solution

Various peptide lipids were dissolved to give various 1.3 mM aqueous peptide lipid solutions (1.0 ml) and dispersed by sonication.

Example 2

Introduction of Plasmid DNA into Cultured Cells Using Peptide Lipids Having Various Head Lengths Cultured cells (CHO cells, HC cells) ($1 \times 10^5$ cells/well) were preincubated in a 24 well plate for 24 hr (CHO cells; 10% FBS-containing DMEM medium, HC cells; 10% FBS-containing DMEM/F-12 medium), and the medium was exchanged with 0.5 ml of a fresh 10% FBS-containing medium upon introduction.

Figure 1B:
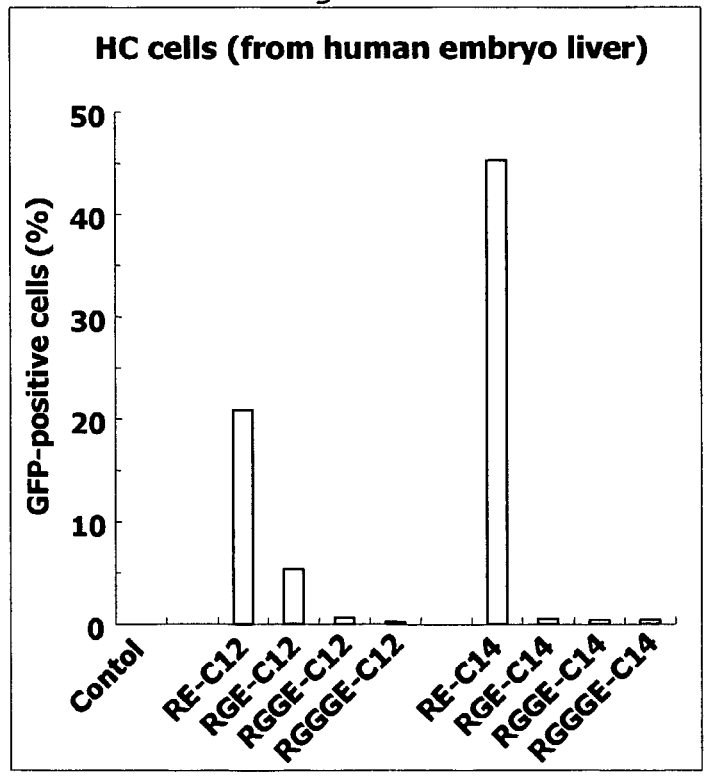

Plasmid DNA (pCMV-IE-hsGFP; purchased from NIPPON GENE CO., LTD., 1 µg per well) was mixed with 25 µl of 150 mM NaCl solution. Various 1.3 mM peptide lipids (RE-C12, RGE-C12, RGGE-C12, RGGGE-C12, RE-C14, RGE-C14, RGGE-C14, RGGGE-C14, each 5 µl) were mixed with the above-mentioned plasmid DNA solution and the mixtures were incubated for 5 min to give peptide lipid—DNA complexes. The complexes were added to the above-mentioned cells and the mixtures were cultured in a 5% CO$_2$ incubator at 37° C. for 24 hr. The next day, the cells were observed with a fluorescence microscope and fluorescent cells were measured by a flow cytometer. The results are shown in FIG. 1. It was found that the use of a peptide lipid as a carrier resulted in the highly frequent expression of GFP in the cells and highly efficient introduction of plasmid DNA into the cells.

Example 3

Cytotoxicity by Introduction of siRNA into Cultured Cells Using Various Concentrations of Peptide Lipid Cultured cells (CHO-EGFP cells; CHO cells which express constitutively fluorescent protein EGFP, and which were prepared by a conventional method) ($1 \times 10^5$ cells/well) were preincubated in a 24 well plate for 24 hr (10% FBS-containing DMEM medium), and the medium was exchanged with 0.5 ml of a fresh 10% FBS-containing medium upon introduction.

Figure 2:
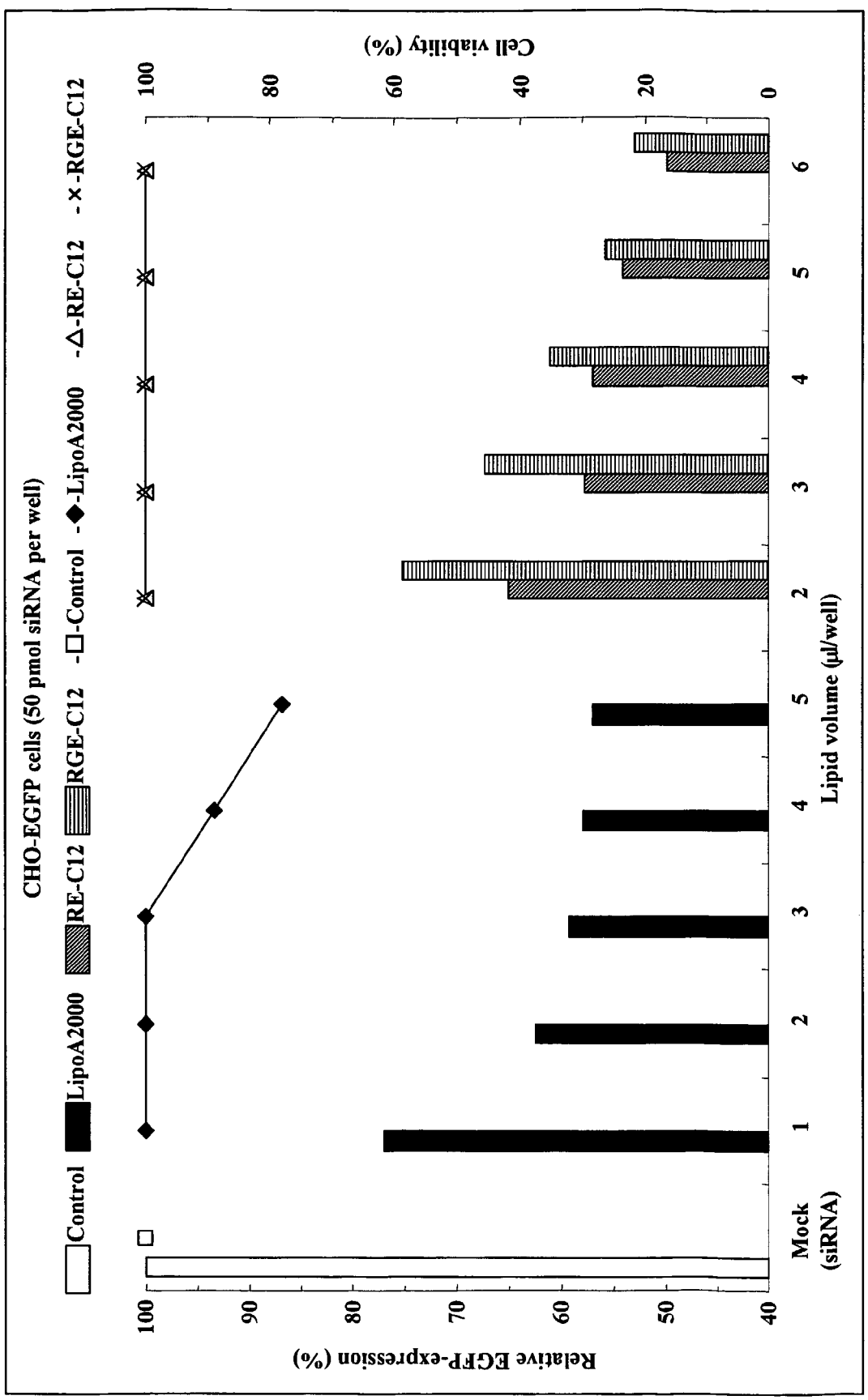
FIG. 2 shows dose-dependencies of peptide lipids of the present invention and Lipofectamine 2000 in introduction efficiency of siRNA into and cytotoxicity to CHO-EGFP cells, wherein bar graphs show relative EGFP expression (%) and line graphs show cell viability (%).

Anti-EGFP-siRNA (purchased from NIPPON GENE CO., LTD., 50 μmol per well) was mixed with 25 μl of 150 mM NaCl solution (for peptide lipids) and DMEM medium (125 μl) (for Lipofectamine 2000), respectively. Various 1.3 mM peptide lipids (RE-C12, RGE-C12, each 2-6 μl) and Lipofectamine 2000 (purchased from Invitrogen; LipoA2000) (1-5 μl) were mixed with the above-mentioned siRNA solutions and the mixtures were incubated for 5 min to give RE-C12—RNA complex, RGE-C12—RNA complex and Lipofectamine 2000—RNA complex. The complexes were added to the above-mentioned cells and the mixtures were cultured in a 5% $CO_2$ incubator at 37° C. for 24 hr. The next day, the cells were observed with a microscope and cell death was determined by trypan blue staining. The results are shown in FIG. 2. When peptide lipid was used as a carrier, cytotoxicity was not observed at all, no significant difference from non-introduction cells was found in the cell viability, and therefore, peptide lipid was found to have low cytotoxicity. Furthermore, when peptide lipid was used as a carrier, EGFP expression was remarkably suppressed by siRNA, where its ability was equivalent to or higher than that of Lipofectamine 2000, and it was found that siRNA was highly efficiently introduced into the cells.

Example 4

Introduction of siRNA into Cultured Cells Using Peptide Lipids Having Various Head Lengths Cultured cells (CHO-EGFP cells; CHO cells which express constitutively fluorescent protein EGFP, and which were prepared by a conventional method) ($1 \times 10^5$ cells/well) were preincubated in a 24 well plate for 24 hr (10% FBS-containing DMEM medium), and the medium was exchanged with 0.5 ml of a fresh 10% FBS-containing medium upon introduction.

Figure 3:
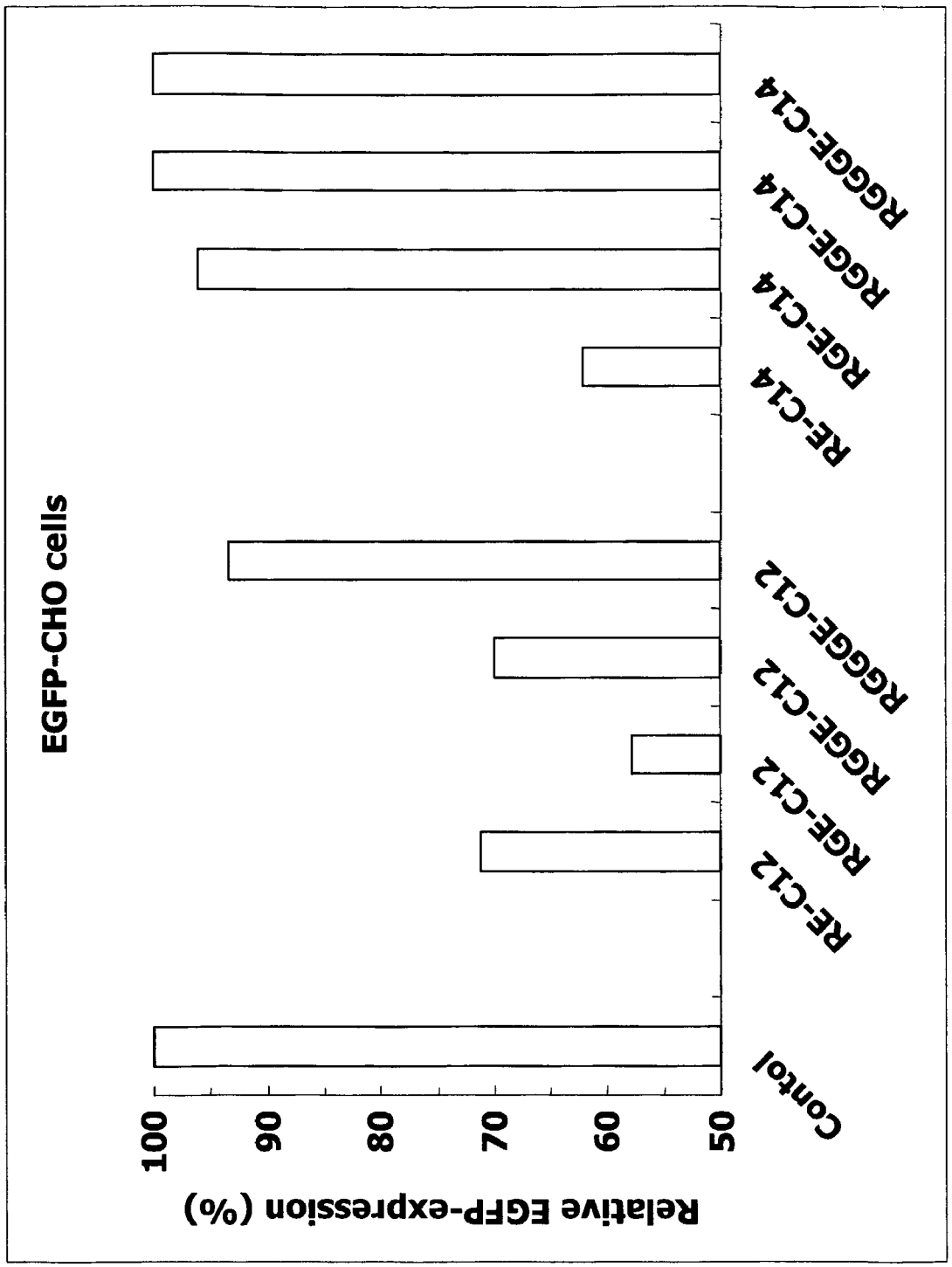
FIG. 3 shows an effect of head length of peptide lipids on introduction efficiency of siRNA into CHO-EGFP cells.

Anti-EGFP-siRNA (purchased from NIPPON GENE CO., LTD., 50 μmol per well) was mixed with 25 μl of 150 mM NaCl solution. Various 1.3 mM peptide lipids (RE-C12, RGE-C12, RGGE-C12, RGGGE-C12, RE-C14, RGE-C14, RGGE-C14, RGGGE-C14, each 5 μl) were mixed with the above-mentioned siRNA solution and the mixtures were incubated for 5 min to give peptide lipid—RNA complexes. The complexes were added to the above-mentioned cells and the mixtures were cultured in a 5% $CO_2$ incubator at 37° C. for 24 hr. The next day, the cells were observed with a fluorescence microscope and fluorescence cells were measured by a flow cytometer. The results are shown in FIG. 3. When peptide lipid was used as a carrier, EGFP expression was remarkably suppressed by siRNA, and it was found that siRNA was highly efficiently introduced into the cells.

Example 5

Introduction of Plasmid DNA into Cultured Cells Using Peptide Lipids Having Basic Amino Acid Head Cultured cells (CHO cells) ($1 \times 10^5$ cells/well) were preincubated in a 24 well plate for 24 hr (10% FBS-containing DMEM medium), and the medium was exchanged with 0.5 ml of a fresh 10% FBS-containing medium upon introduction.

Figure 4:
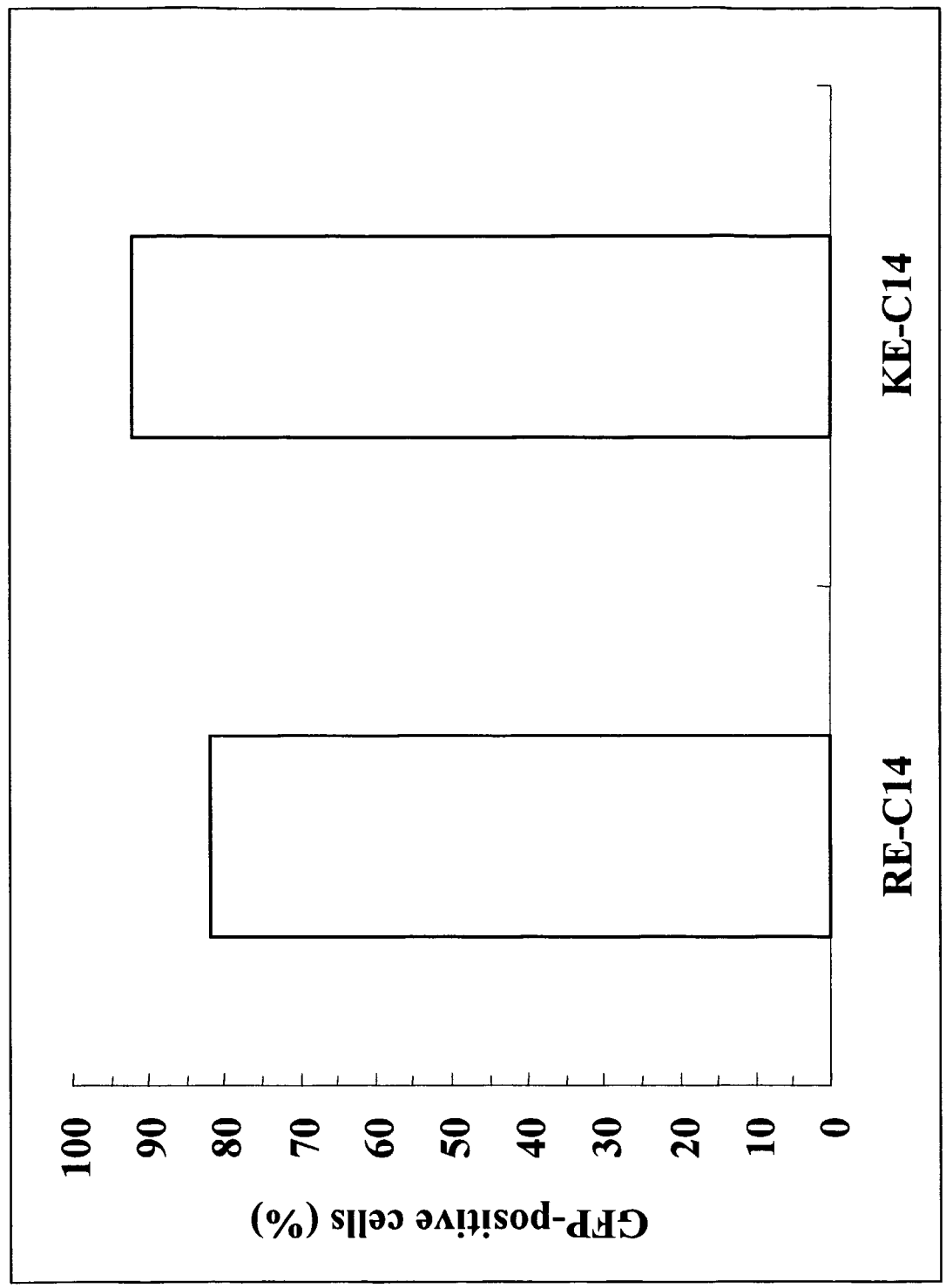
FIG. 4 shows an effect of peptide lipids having a basic amino acid head on introduction efficiency of plasmid DNA into cells.

Plasmid DNA (pCMV-IE-hsGFP, purchased from NIPPON GENE CO., LTD., 1 μg per well) was mixed with 25 μl of 150 mM NaCl solution. Various 1.3 mM peptide lipids (RE-C14, KE-C14, each 5 μl) were mixed with the above-mentioned plasmid DNA solution and the mixtures were incubated for 5 min to give peptide lipid—DNA complexes. The complexes were added to the above-mentioned cells and the mixtures were cultured in a 5% $CO_2$ incubator at 37° C. for 24 hr. The next day, the cells were observed with a fluorescence microscope and fluorescent cells were measured with a flow cytometer. The results are shown in FIG. 4. When peptide lipids where Arg or Lys was designed as a head were used, GFP was highly frequently expressed in the cells for both lipids, and it was found that plasmid DNA was highly efficiently introduced into the cells.

Example 6

Introduction of siRNA into Cultured Cells Using Peptide Lipids Having Various Connectors Cultured cells (CHO-EGFP cells; CHO cells which express constitutively fluorescent protein EGFP, and which were prepared by a conventional method) ($1 \times 10^5$ cells/well) were preincubated in a 24 well plate for 24 hr (10% FBS-containing DMEM medium), and the medium was exchanged with 0.5 ml of a fresh 10% FBS-containing medium upon introduction.

Figure 5:
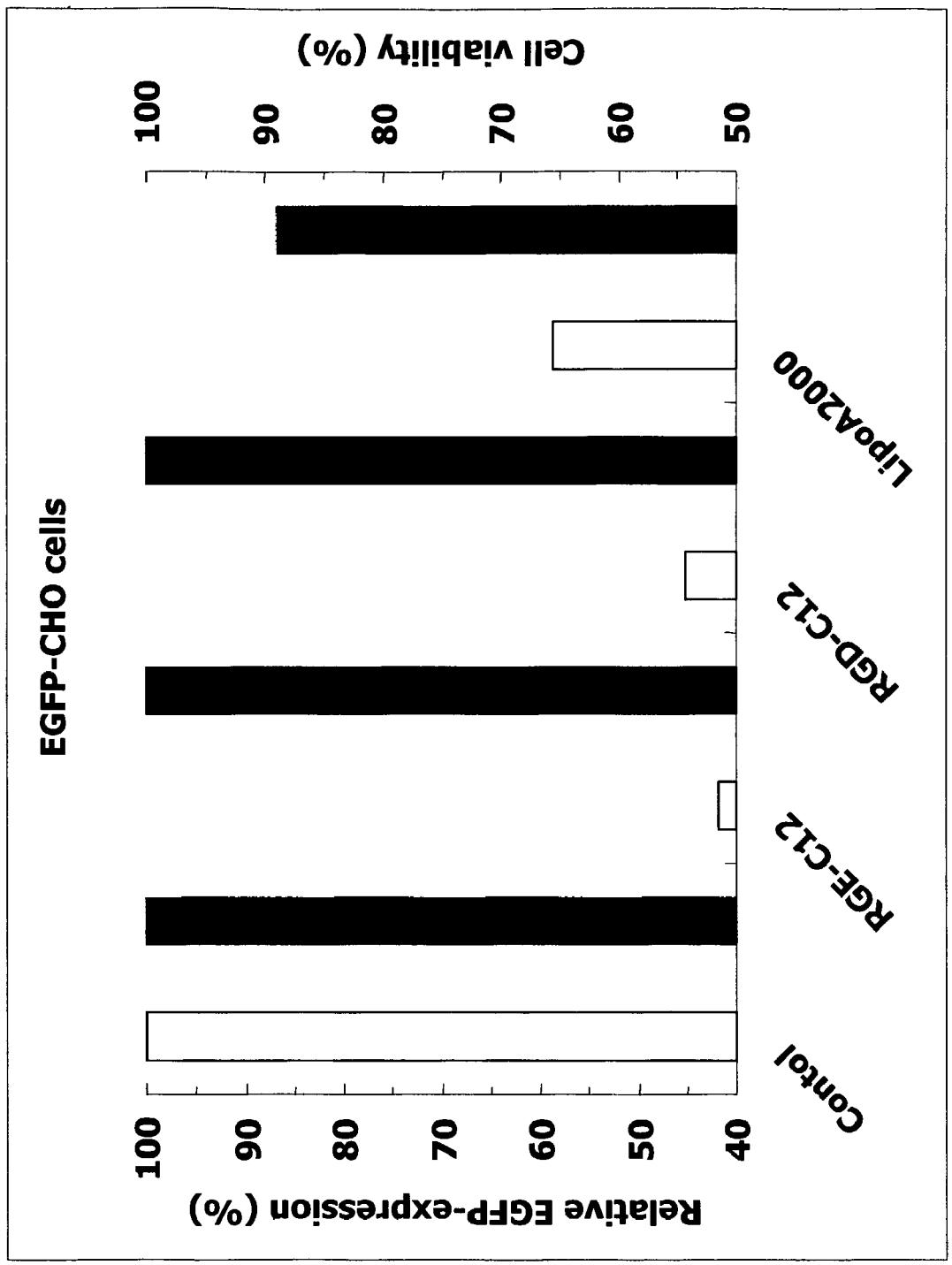
FIG. 5 shows effects of peptide lipids having various connectors on introduction efficiency of siRNA into and cytotoxicity to CHO-EGFP cells, wherein white bars show relative EGFP expression (%) and black bars show cell viability (%).

Anti-EGFP-siRNA (purchased from NIPPON GENE CO., LTD., 50 μmol per well) was mixed with 25 μl of 150 mM NaCl solution. Various 1.3 mM peptide lipids (RGE-C12, RGD-C12, each 5 μl) and Lipofectamine 2000 (purchased from Invitrogen; LipoA2000) (5 μl) were mixed with the above-mentioned siRNA solution and the mixtures were incubated for 5 min to give RGE-C12—RNA complex, RGD-C12—RNA complex and Lipofectamine 2000—RNA complex. The complexes were added to the above-mentioned cells and the mixture was cultured in a 5% $CO_2$ incubator at 37° C. for 24 hr. The next day, the cells were observed with a fluorescence microscope and fluorescence cells were measured by a flow cytometer. The results are shown in FIG. 5. When peptide lipids designed to have Glu or Asp as a connector were used, EGFP expression was remarkably suppressed by siRNA, siRNA was highly efficiently expressed in the cells, where their abilities were higher than the ability of Lipofectamine 2000, and it was found that they were superior in cytotoxicity.

Example 7

Introduction of Plasmid DNA into Cultured Cells Using Peptide Lipids Having Various Tail Lengths Cultured cells (CHO cells, HC cells) ($1 \times 10^5$ cells/well) were preincubated in a 24 well plate for 24 hr (CHO cells; 10% FBS-containing DMEM medium, HC cells; 10% FBS-containing DMEM/F-12 medium), and the medium was exchanged with 0.5 ml of a fresh 10% FBS-containing medium upon introduction.

Figure 6A:
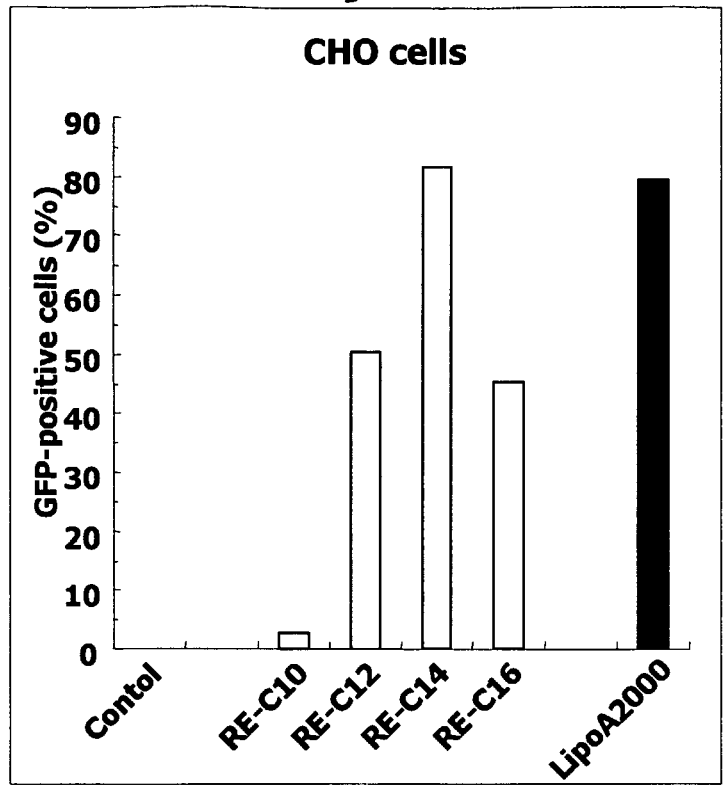
FIG. 6 shows an effect of tail length of peptide lipids on introduction efficiency of plasmid DNA into CHO cells (FIG. 6A) and HC cells (FIG. 6B).
Figure 6B:
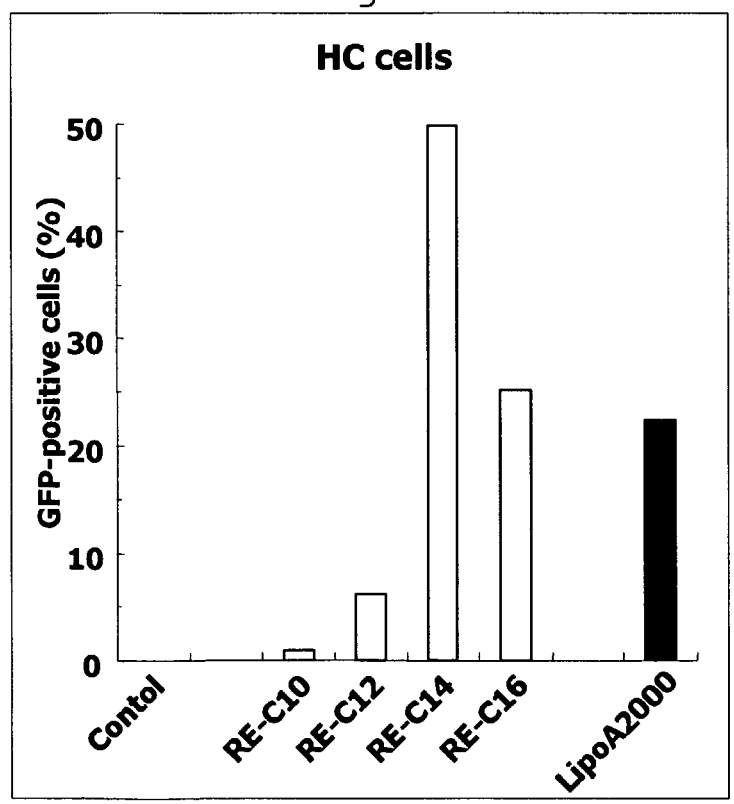

Plasmid DNA (pCMV-IE-hsGFP, purchased from NIPPON GENE CO., LTD., 1 μg per well) was mixed with 25 μl of 150 mM NaCl solution (for peptide lipids) and DMEM medium (125 μl) (for Lipofectamine 2000), respectively. Various 1.3 mM peptide lipids (RE-C10, RE-C12, RE-C14, RE-C16, each 5 μl) and Lipofectamine 2000 (purchased from Invitrogen; LipoA2000) (2.5 μl, according to protocol) were mixed with the above-mentioned DNA solutions and the mixtures were incubated for 5 min to give RE-C10—DNA complex, RE-C12—DNA complex, RE-C14—DNA complex, RE-C16—DNA complex and Lipofectamine 2000—DNA complex. The complexes were added to the above-mentioned cells and the mixtures were cultured in a 5% $CO_2$ incubator at 37° C. for 24 hr. The next day, the cells were observed with a fluorescence microscope and fluorescence cells were measured by a flow cytometer. The results are shown in FIG. 6. When peptide lipids designed to have a tail length of C10 to C16 were used, GFP was expressed in the cells, and it was found that plasmid DNA was highly efficiently introduced into the cells.

Example 8

Introduction of Plasmid DNA into Cultured Cells Using Peptide Lipid Having an Unsaturated Hydrocarbon Group for Tail Cultured cells (CHO cells) ($1 \times 10^5$ cells/well) were preincubated in a 24 well plate for 24 hr (10% FBS-containing DMEM medium), and the medium was exchanged with 0.5 ml of a fresh 10% FBS-containing medium upon introduction.

Figure 7:
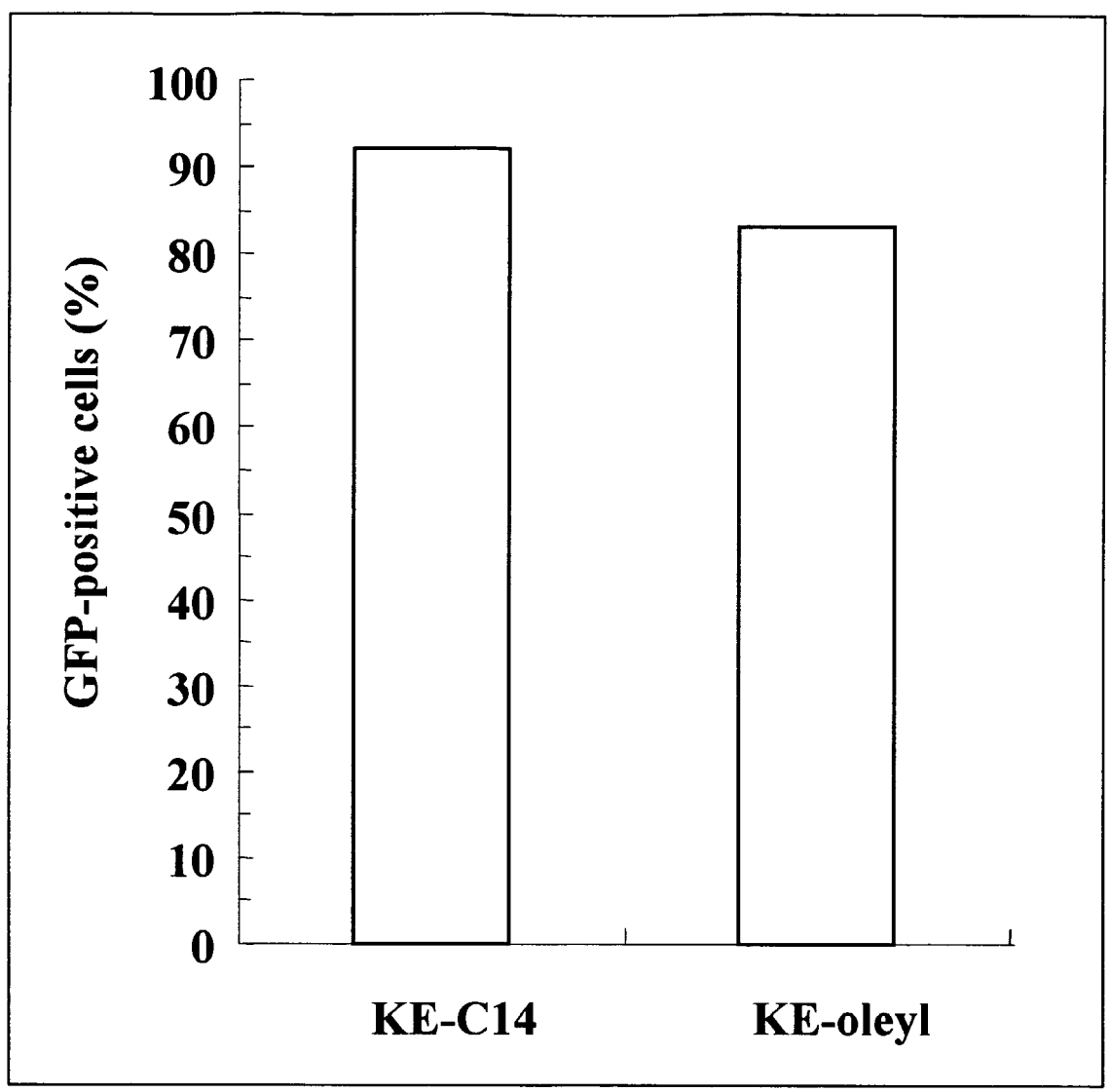
FIG. 7 shows an effect of a peptide lipid having an unsaturated hydrocarbon group on introduction efficiency of plasmid DNA into cells.

Plasmid DNA (pCMV-IE-hsGFP, purchased from NIPPON GENE CO., LTD., 1 μg per well) was mixed with 25 μl of 150 mM NaCl solution. Various 1.3 mM peptide lipids (KE-C14, KE-oleyl, each 5 μl) were mixed with the above-mentioned plasmid DNA solution and the mixtures were incubated for 5 min to give peptide lipid—DNA complexes. The complexes were added to the above-mentioned cells and the mixtures were cultured in a 5% $CO_2$ incubator at 37° C. for 24 hr. The next day, the cells were observed with a fluorescence microscope and fluorescence cells were measured by a flow cytometer. The results are shown in FIG. 7. When peptide lipids designed to have an unsaturated hydrocarbon group as a tail were used, GFP was also expressed in the cells, and it was found that plasmid DNA was highly efficiently introduced into the cells.

Example 9

Introduction of Plasmid DNA into Cultured Cells Using Peptide Lipid Having Dendrimer Type Amino Acid Sequence Cultured cells (CHO cells) ($1 \times 10^5$ cells/well) were preincubated in a 24 well plate for 24 hr (10% FBS-containing DMEM medium), and the medium was exchanged with 0.5 ml of a fresh 10% FBS-containing medium upon introduction.

Figure 8:
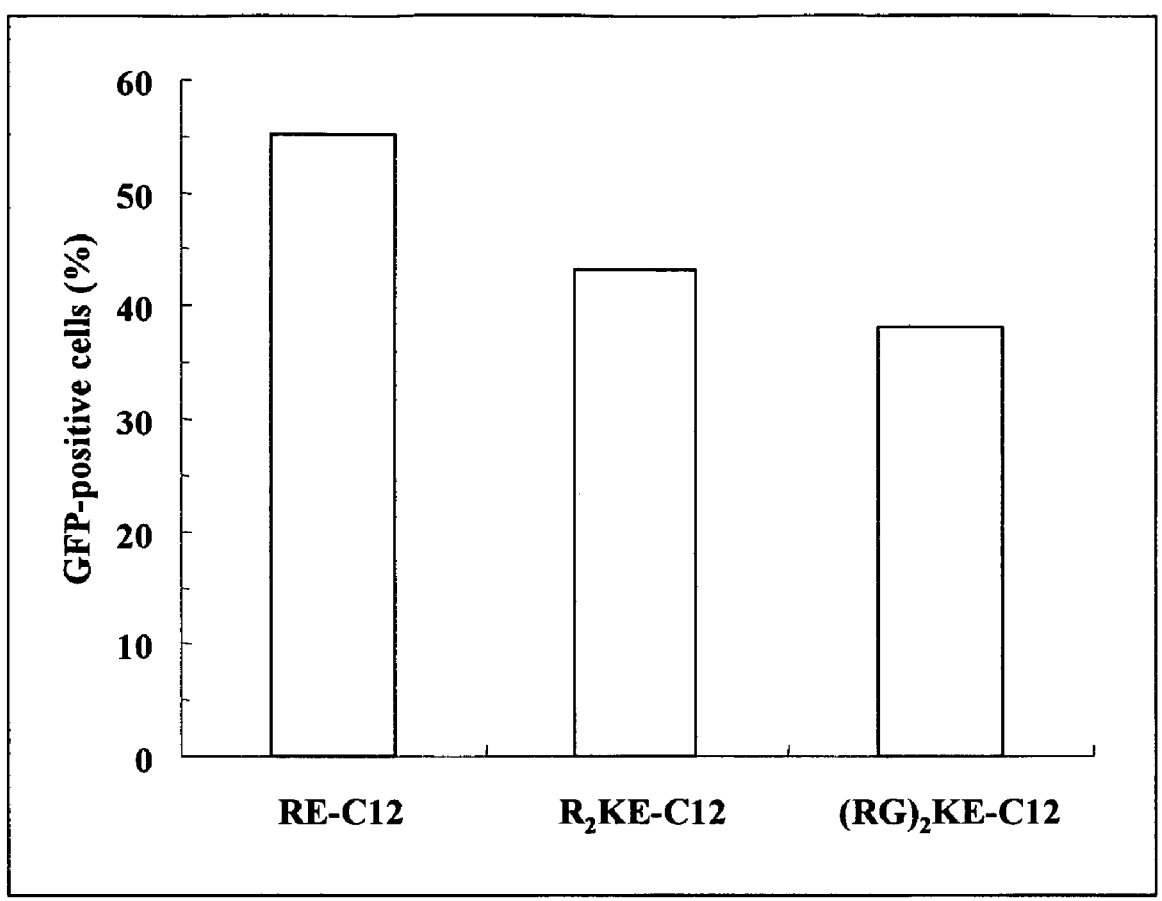
FIG. 8 shows an effect of peptide lipids having a dendrimer type amino acid sequence on introduction efficiency of plasmid DNA into cells.

Plasmid DNA (pCMV-IE-hsGFP, purchased from NIPPON GENE CO., LTD., 1 μg per well) was mixed with 25 μl of 150 mM NaCl solution. Various 1.3 mM peptide lipids (RE-C12, $R_2$KE-C12, $(RG)_2$KE-C12, each 5 μl) were mixed with the above-mentioned plasmid DNA solution and the mixtures were incubated for 5 min to give peptide lipid—DNA complexes. The complexes were added to the above-mentioned cells and the mixtures were cultured in a 5% $CO_2$ incubator at 37° C. for 24 hr. The next day, the cells were observed with a fluorescence microscope and fluorescence cells were measured by a flow cytometer. The results are shown in FIG. 8. When peptide lipids designed to have a dendrimer type amino acid sequence as a head were used, too, GFP was expressed in the cells, and it was found that plasmid DNA was highly efficiently introduced into the cells.

Example 10

Introduction of siRNA into Mouse Using Peptide Lipid

Cy3-labeled siRNA (400 μmol, purchased from Dharmacon) was mixed with 200 μl of 150 mM NaCl solution, 1.3 mM peptide lipid (RE-C12) (16 μl) was mixed with the above-mentioned siRNA solution and the mixture was incubated for 5 min to give peptide lipid—RNA complex. This was injected to Balb/c mouse (15-week-old) from the tail vein. In the mouse, acute toxicity was not observed at the concentration tested. Four hours later, the mouse was autopsied and each tissue (heart, lung, liver, kidney, spleen) was removed, which was cut into small pieces and observed with a fluorescence microscope. The results are shown in Table 1. When peptide lipid was used as a carrier, siRNA could be introduced into each tissue in the body. Introduction efficiency into the liver and spleen was particularly superior.

TABLE 1

Effect of introduction of siRNA into mouse using peptide lipid

| organ | evaluation |
| --- | --- |
| heart | 5% |
| lung | 10% |
| liver | 25% |
| kidney | 5% |
| spleen | 30% |

INDUSTRIAL APPLICABILITY

Since the carrier of the present invention shows low cytotoxicity and is highly efficient in the intracellular introduction of a compound, it is useful as a reagent for highly efficient intracellular introduction of a compound for research and pharmaceutical use.

The invention claimed is:

1. A compound selected from

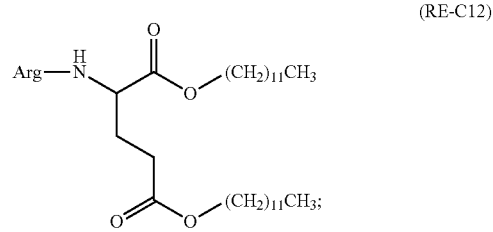

(RE-C12)

(RGE-C12)
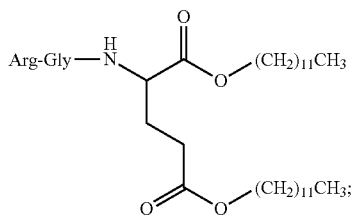

(RE-C14)
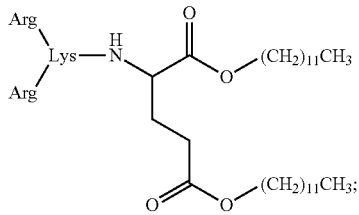

(KE-C14)

(RGD-C12)

(RE-C16)

(KEC18-oleyl)

(R₂KE-C12)
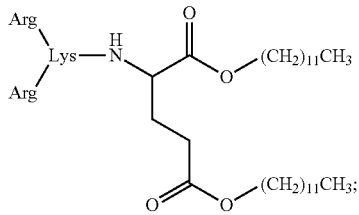

((RG)₂KE-C12)
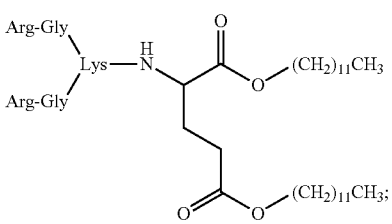

(KE-C12)
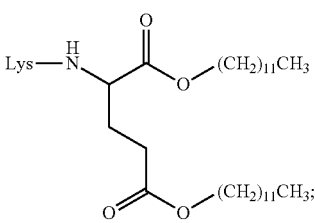

(KGE-C12)
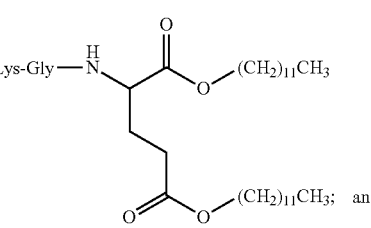

and (KE-C18)
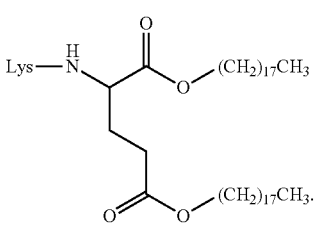

2. A carrier for introducing a compound of interest into a cell, which comprises the compound of claim 1.

3. The carrier of claim 2, wherein the compound of interest is a nucleic acid.

4. The carrier of claim 3, wherein the nucleic acid is a plasmid DNA, cDNA or antisense DNA, or an siRNA, miRNA, shRNA, mRNA, antisense RNA or RNA replicon.

5. The carrier of claim 2, wherein the compound of interest is a peptide or protein.

6. A complex of the carrier of claim 2 and a compound of interest.

7. A method for introducing a compound of interest into a cell, which comprises contacting the complex of claim 6 with the cell.

8. A method for introducing a compound of interest into a cell within a human or non-human subject, which comprises administering the complex of claim 6 to the subject.

9. The compound of claim 1 that is
(RE-C12)
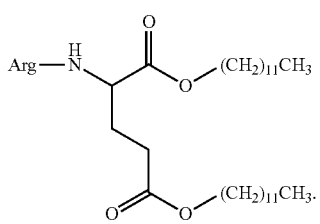
10. The compound of claim 1 that is
(RGE-C12)
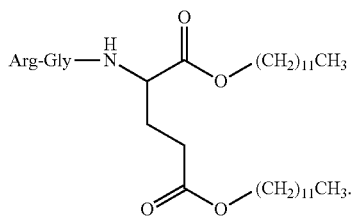
11. The compound of claim 1 that is
(RE-C14)
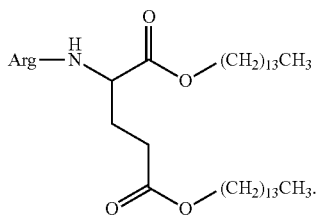
12. The compound of claim 1 that is
(KE-C14)
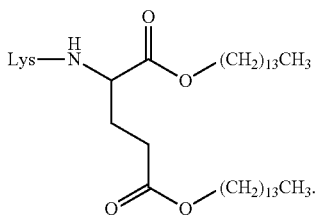
13. The compound of claim 1 that is
(RGD-C12)
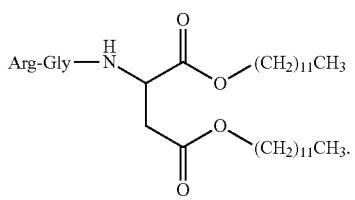
14. The compound of claim 1 that is
(RE-C16)
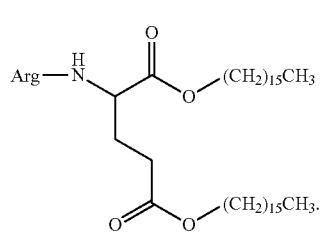
15. The compound of claim 1 that is
(KEC18-oleyl)
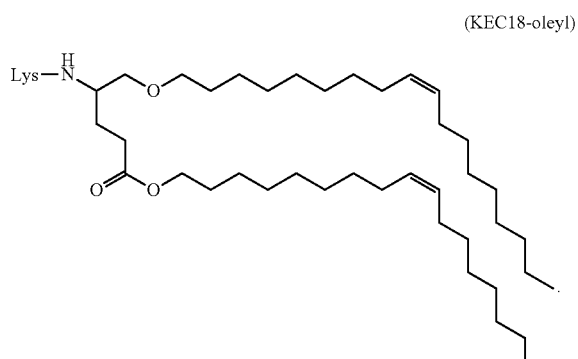
16. The compound of claim 1 that is
(R$_2$KE-C12)
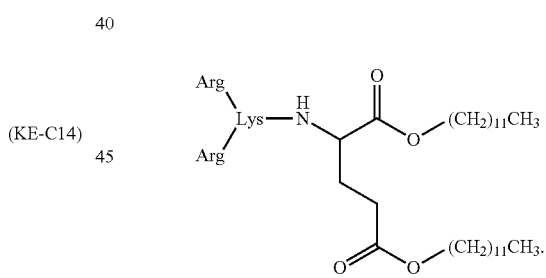
17. The compound of claim 1 that is
((RG)$_2$KE-C12)
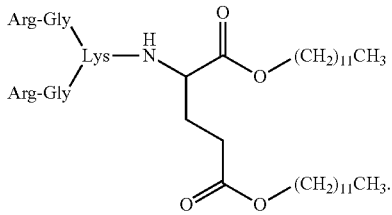

18. The compound of claim 1 that is
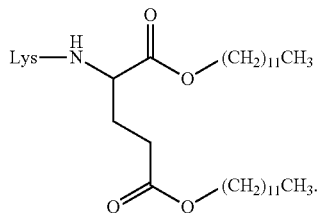
(KE-C12)
19. The compound of claim 1 that is
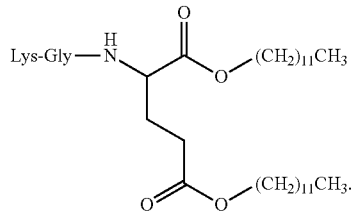
(KGE-C12)
20. The compound of claim 1 that is
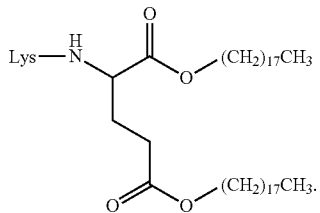
(KE-C18)
* * * * *

UNITED STATES PATENT AND TRADEMARK OFFICE
CERTIFICATE OF CORRECTION

PATENT NO. : 8,299,129 B2  
APPLICATION NO. : 12/281227  
DATED : October 30, 2012  
INVENTOR(S) : Kusumoto et al.

It is certified that error appears in the above-identified patent and that said Letters Patent is hereby corrected as shown below:

*In the Claims*

Column 26, claim 15, lines 20-35, the formula should read:

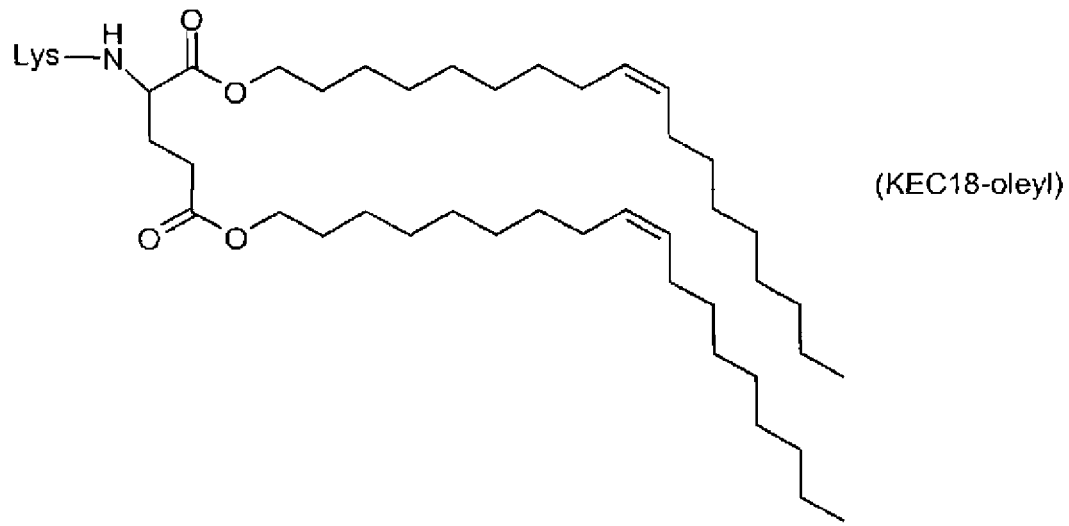

Signed and Sealed this  
Twenty-first Day of May, 2013

Teresa Stanek Rea  
*Acting Director of the United States Patent and Trademark Office*